（12） United States Patent
Parks et al.

(10) Patent No.: US 10,544,430 B2
(45) Date of Patent: Jan. 28, 2020

(54) VESICULAR STOMATITIS VIRUS AND VIRUS RESCUE SYSTEM

(71) Applicant: International AIDS Vaccine Initiative, New York, NY (US)

(72) Inventors: Christopher L. Parks, Boonton, NJ (US); Maoli Yuan, Brooklyn, NY (US); Kevin Wright, Brooklyn, NY (US); Christy Jurgens, Rahway, NJ (US)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

(21) Appl. No.: 15/417,256

(22) Filed: Jan. 27, 2017

(65) Prior Publication Data
US 2017/0198305 A1    Jul. 13, 2017

Related U.S. Application Data

(63) Continuation of application No. 13/623,437, filed on Sep. 20, 2012, now abandoned.

(60) Provisional application No. 61/537,497, filed on Sep. 21, 2011.

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2760/20221* (2013.01); *C12N 2760/20243* (2013.01); *C12N 2800/22* (2013.01)

(58) Field of Classification Search
None
See application file for complete search history.

(56) References Cited

U.S. PATENT DOCUMENTS

2008/0286848 A1    11/2008  Skiadopoulos et al.

OTHER PUBLICATIONS

Kenny et al. The cysteine knot of platelet glycoprotein Ibb (GPIbb) is critical for the interaction of GPIb with GPIX. Blood. 2002;99: 4428-4433.*
GenBank: AF473864.1. Vesicular stomatitis Indiana virus strain 98COE, complete genome. dated Sep. 24, 2002.*
Baklanov, et al. "Effect on DNA transcription of nucleotide sequences upstream to T7 promoter" Nucleic Acids Research, 1996, 24(18):3659-3660.
Chowrira, et al. "In Vitro and in Vivo Comparison of Hammerhead, Hairpin, and Hepatitis Delta Virus Self-processing Ribozyme Cassettes" The Journal of Biological Chemistry, 1994, 269(41):25856-25864.
Inoue, et al. "An improved method for recovering rabies virus from cloned cDNA" Journal of Virological Methods, 2003, 107:229-236.
Lopez, et al. "The Low Processivity of T7 RNA Polymerase Over the Initially Transcribed Sequence Can Limit Productive Initiation in Vivo" J. Mol. Biol., 1997, 269:41-51.
Ternette, et al. "Expression of RNA virus proteins by RNA polymerase II dependent expression plasmids is hindered at multiple steps" Virology Journal, 2007, 4:51.
Witko, et al. "An Efficient Helper-Virus-Free Method for Rescue of Recombinant Paramyxoviruses and Rhadoviruses From a Cell Line Suitable for Vaccine Development" Journal of Virological Methods, 2006, 135:91-101.

* cited by examiner

*Primary Examiner* — Nianxiang Zou
(74) *Attorney, Agent, or Firm* — Duane Morris LLP; Thomas J. Kowalski; Deborah L. Lu

(57) ABSTRACT

The present relation relates to recombinant vesicular stomatitis virus for use as prophylactic and therapeutic vaccines as well as the preparation and purification of immunogenic compositions which are formulated into the vaccines of the present invention.

18 Claims, 14 Drawing Sheets

Specification includes a Sequence Listing.

GENOME FRAGMENT VSV-A/G (1489 bp)
atagtcgagacgACGAAGACAAACAAACCATTATTATCATTAAAAGGCTC
AGGAGAAACTTTAACAGTAATCAAATGTCTGTTACAGTCAAGAGAATCA
TTGACAACACAGTCATAGTTCCAAAACTTCCTGCAAATGAGGATCCAGTG
GAATACCCGGCAGATTACTTCAGAAAATCAAAGGAGATTCCTCTTTACAT
CAATACTACAAAAAGTTTGTCAGATCTAAGAGGATATGTCTACCAAGGCC
TCAAATCCGGAAATGTATCAATCATACATGTCAACAGCTACTTGTATGGA
GCATTGAAGGACATCCGGGGTAAGTTGGATAAAGATTGGTCAAGTTTCGG
AATAAACATCGGGAAGGCAGGGGATACAATCGGAATATTTGACCTTGTAT
CCTTGAAAGCCCTGGACGGTGTACTTCCAGATGGAGTATCGGATGCTTCC
AGAACCAGCGCAGATGACAAATGGTTGCCTTTGTATCTACTTGGCTTATA
CAGAGTGGGCAGAACACAAATGCCTGAATACAGAAAAGGCTCATGGATG
GGCTGACAAATCAATGCAAAATGATCAATGAACAGTTTGAACCTCTTGTG
CCAGAAGGTCGTGACATTTTTGATGTGTGGGGAAATGACAGTAATTACAC
AAAAATTGTCGCTGCAGTGGACATGTTCTTCCACATGTTCAAAAAACATG
AATGTGCCTCGTTCAGATACGGAACTATTGTTTCCAGATTCAAAGATTGT
GCTGCATTGGCAACATTTGGACACCTCTGCAAAATAACCGGAATGTCTAC
AGAAGATGTGACGACCTGGATCTTGAACCGGAAGTTGCAGATGAGATGG
TCCAAATGATGCTTCCAGGCCAAGAAATTGACAAGGCTGATTCATACATG
CCTTATTTGATCGACTTTGGATTGTCTTCTAAGTCTCCATATTCTTCCGT
CAAAAACCCTGCCTTCCACTTCTGGGGCAATTGACAGCTCTTCTGCTCA
GATCCACCAGAGCAAGGAATGCCCGACAGCCTGATGACATTGAGTATACA
TCTCTTACTACAGCAGGTTTGTTGTACGCTTATGCAGTAGGATCCTCTGC
TGACTTGGCACAACAGTTTTGTGTTGGAGATAGCAAATACACTCCAGATG
ATAGTACCGGAGGATTGACGACTAATGCACCGCCACAAGGCAGAGATGTG
GTCGAATGGCTCGGATGGTTTGAAGATCAAAACAGAAAACCGACTCCTGA
TATGATGCAGTATGCGAAACGAGCAGTCATGTCACTGCAAGGCCTAAGAG
AGAAGACAATTGGCAAGTATGCTAAGTCAGAGTTTGACAAATGACCCTAT
AATTCTCAGATCACCTATTATATATTATGCTAGCTTGTTCGAACTCTTAA
TTAACGCCCCGAGTATGTCGACGTACTTAAGACCCTCTTGTGGTTTTTAT
TTTTTATCTGGTTTTGTGGTCTTCGTcgtctccggccgg

FIG. 2B

GENOME FRAGMENT B  (1645 bp)
gctagctatgaaaaaaactaacagatatcATGGATAATCTCACAAAAGTT
CGTGAGTATCTCAAGTCCTATTCTCGTCTAGATCAGGCGGTAGGAGAGAT
AGATGAGATCGAAGCACAACGAGCTGAAAAGTCCAATTATGAGTTGTTCC
AAGAGGACGGAGTGGAAGAGCATACTAGGCCCTCTTATTTTCAGGCAGCA
GATGATTCTGACACAGAATCTGAACCAGAAATTGAAGACAATCAAGGCTT
GTATGTACCAGATCCGGAAGCTGAGCAAGTTGAAGGCTTTATACAGGGGC
CTTTAGATGACTATGCAGATGAGGACGTGGATGTTGTATTCACTTCGGAC
TGGAAACAGCCTGAGCTTGAATCCGACGAGCATGGAAAGACCTTACGGTT
GACATTGCCAGAGGGTTTAAGTGGAGAGCAGAAATCCCAGTGGCTTTTGA
CGATTAAAGCAGTCGTTCAAAGTGCCAAACACTGGAATCTGGCAGAGTGC
ACATTTGAAGCATCGGGAGAAGGGGTCATCATAAAAAAGCGCCAGATAAC
TCCGGATGTATATAAGGTCACTCCAGTGATGAACACACATCCGTcCCAAT
CAGAAGCCGTATCAGATGTTTGGTCTCTCTCAAAGACATCCATGACTTTC
CAACCCAAGAAAGCAAGTCTTCAGCCTCTCACCATATCCTTGGATGAATT
GTTCTCATCTAGAGGAGAATTCATCTCTGTCGGAGGTAACGGACGAATGT
CTCATAAAGAGGCCATCCTGCTCGGTCTGAGGTACAAAAAGTTGTACAAT
CAGGCGAGAGTCAAATATTCTCTGTAGactagtatgaaaaaaagtaacag
atatcacaatctaagtgttatcccaatccattcatcATGAGTTCCTTAAA
GAAGATTCTCGGTCTGAAGGGGAAAGGTAAGAAATCTAAGAAATTAGGGA
TCGCACCACCCCCTTATGAAGAGGACACTAACATGGAGTATGCTCCGAGC
GCTCCAATTGACAAATCCTATTTTGGAGTTGACGAGATGGACACTCATGA
TCCGAATCAATTAAGATATGAGAAATTCTTCTTTACAGTGAAAATGACGG
TTAGATCTAATCGTCCGTTCAGAACATACTCAGATGTGGCAGCCGCTGTA
TCCCATTGGGATCACATGTACATCGGAATGGCAGGGAAACGTCCCTTCTA
CAAGATCTTGGCTTTTTTGGGTTCTTCTAATCTAAAGGCCACTCCAGCGG
TATTGGCAGATCAAGGTCAACCAGAGTATCATGCTCACTGTGAAGGCAGG
GCTTATTTGCCACACAGAATGGGGAAGACCCCTCCCATGCTCAATGTACC
AGAGCACTTCAGAAGACCATTCAATATAGGTCTTTACAAGGGAACGATTG
AGCTCACAATGACCATCTACGATGATGAGTCACTGGAAGCAGCTCCTATG
ATCTGGGATCATTTCAATTCTTCCAAATTTTCTGATTTCAGAGAGAAGGC
CTTAATGTTTGGCCTGATTGTCGAGAAAAAGGCATCTGGAGCTTGGGTCC
TGGATTCTGTCAGCCACTTCAAATGAgctagtctagcttccagcttctga
Acaatccccggtttactcagtctctcctaattccagcctttcgaa

FIG. 2C

GENOME FRAGMENT C (1689 bp)
ttcgaacaactaatatcctgtcttctctatccctatgaaaaaaactaaca
gagatcgatctgtttccttgacaccATGAAGTGCCTTTTGTACTTAGCTT
TTTTATTCATCGGGGTGAATTGCAAGTTCACCATAGTTTTTCCACACAAC
CAAAAAGGAAACTGGAAAAATGTTCCTTCCAATTACCATTATTGCCCGTC
AAGCTCAGATTTAAATTGGCATAATGACTTAaTAGGCACAGCCTTACAAG
TCAAAATGCCCAAGAGTCACAAGGCTATTCAAGCAGACGGTTGGATGTGT
CATGCTTCCAAATGGGTCACTACTTGTGATTTCCGCTGGTACGGACCGAA
GTATATAACACATTCCATCCGATCCTTCACTCCATCTGTAGAACAATGCA
AGGAAAGCATTGAACAAACGAAACAAGGAACTTGGCTGAATCCAGGCTTC
CCTCCTCAAAGTTGTGGATATGCAACTGTGACGGATGCTGAAGCAGCGAT
TGTCCAGGTGACTCCTCACCATGTGCTTGTTGATGAATACACAGGAGAAT
GGGTTGATTCACAGTTCATCAACGGAAAATGCAGCAATGACATATGCCCC
ACTGTCCATAACTCCACAACCTGGCATTCCGACTATAAGGTCAAAGGGCT
ATGTGATTCTAACCTCATTTCCATGGACATCACCTTCTTCTCAGAGGACG
GAGAGCTATCATCCCTAGGAAAGgAGGGCACAGGGTTCAGAAGTAACTAC
TTTGCTTATGAAACTGGAGACAAGGCCTGCAAAATGCAGTACTGCAAGCA
TTGGGGAGTCAGACTCCCATCAGGTGTCTGGTTCGAGATGGCTGATAAGG
ATCTCTTTGCTGCAGCCAGATTCCCTGAATGCCCAGAAGGGTCAAGTATC
TCTGCTCCATCTCAGACCTCAGTGGATGTAAGTCTCATTCAGGACGTTGA
GAGGATCTTGGATTATTCCCTCTGCCAAGAAACCTGGAGCAAAATCAGAG
CGGGTCTTCCCATCTCTCCAGTGGATCTCAGCTATCTTGCTCCTAAAAAC
CCAGGAACCGGTCCTGTCTTTACCATAATCAATGGTACCCTAAAATACTT
TGAGACCAGATACATCAGAGTCGATATTGCTGCTCCAATCCTCTCAAGAA
TGGTCGGAATGATCAGTGGAACTACCACAGAAAGGGaACTGTGGGATGAC
TGGGCTCCATATGAAGACGTGGAAATTGGACCCAATGGAGTTCTGAGGAC
CAGTTCAGGATATAAGTTTCCTTTATATATGATTGGACATGGTATGTTGG
ACTCCGATCTTCATCTTAGCTCAAAGGCTCAGGTGTTTGAACATCCTCAC
ATTCAAGACGCTGCTTCGCAGCTTCCTGATGaTGAGACTTTATTTTTTGG
TGATACTGGGCTATCCAAAAATCCAATCGAGTTTGTAGAAGGTTGGTTCA
GTAGTTGGAAGAGCTCTATTGCCTCTTTTTTCTTTAtCATAGGGTTAATC
ATTGGACTATTCTTGGTTCTCCGAGTTGGTATTTATCTTTGCATTAAATT
AAAGCACACCAAGAAAAGACAGATTTATACAGACATAGAGATGAACCGAC
TTGGAAAGTAActcaaatcctgcacaacagattcttcatgtttgaaccaa
Atcaacttgtgatatcatgctcaaagaggccttaattaa

FIG. 2D

GENOME FRAGMENT D (2851 bp)
ttaattaaattttaattttttatgaaaaaaactaacagcaatcA
TGGAAGTCCACGATTTTGAGACCGACGAGTTCAATGATTTCAATGAAGAT
GACTATGCCACAAGAGAATTCCTGAATCCCGATGAGCGCATGACGTACTT
GAATCATGCTGATTACAATTTGAATTCTCCTCTAATTAGTGATGATATTG
ACAATTTGATCAGGAAATTCAATTCTCTTCCGATTCCCTCGATGTGGGAT
AGTAAGAACTGGGATGGAGTTCTTGAGATGTTAACATCATGTCAAGCCAA
TCCCATCTCAACATCTCAGATGCATAAATGGATGGGAAGTTGGTTAATGT
CTGATAATCATGATGCCAGTCAAGGGTATAGTTTTTTACATGAAGTGGAC
AAAGAGGCAGAAATAACATTTGACGTGGTGGAGACCTTCATCCGCGGCTG
GGGCAACAAACCAATTGAATACATCAAAAAGGAAAGATGGACTGACTCAT
TCAAAATTCTCGCTTATTTGTGTCAAAAGTTTTTGGACTTACACAAGTTG
ACATTAATCTTAAATGCTGTCTCTGAGGTGGAATTGCTCAACTTGGCGAG
GACTTTCAAAGGCAAAGTCAGAAGAAGTTCTCATGGAACGAACATATGCA
GGcTTAGGGTTCCCAGCTTGGGTCCTACTTTTATTTCAGAAGGATGGGCT
TACTTCAAGAAACTTGATATTCTAATGGACCGAAACTTTCTGTTAATGGT
CAAAGATGTGATTATAGGGAGGATGCAAACGGTGCTATCCATGGTATGTA
GAATAGACAACCTGTTCTCAGAGCAAGACATCTTCTCCCTTCTAAATATC
TACAGAATTGGAGATAAAATTGTGGAGAGGCAGGGAAATTTTTCTTATGA
CTTGATTAAAATGGTGGAACCGATATGCAACTTGAAGCTGATGAAATTAG
CAAGAGAATCAAGGCCTTTAGTCCCACAATTCCCTCATTTTGAAAATCAT
ATCAAGACTTCTGTTGATGAAGGGGCAAAAATTGACCGAGGTATAAGATT
CCTCCATGATCAGATAATGAGTGTGAAAACAGTGGATCTCACACTGGTGA
TTTATGGATCGTTCAGACATTGGGGTCATCCTTTTATAGATTATTACgCT
GGACTAGAAAAATTACATTCCCAAGTAACCATGAAGAAAGATATTGATGT
GTCATATGCAAAAGCACTTGCAAGTGATTTAGCTCGGATTGTTCTATTTC
AACAGTTCAATGATCATAAAAAGTGGTTCGTGAATGGAGACTTGCTCCCT
CATGATCATCCCTTTAAAAGTCATGTTAAAGAAAATACATGGCCTACAGC
TGCTCAAGTTCAAGATTTTGGAGATAAATGGCATGAACTTCCGCTGATTA
AATGTTTTGAAATACCCGACTTACTAGACCCATCGATAATATACTCTGAC
AAAAGTCATTCAATGAATAGGTCAGAGGTGTTGAAACATGTCCGAATGAA
TCCGAACACTCCTATCCCTAGTAAAAAGGTGTTGCAGACTATGTTGGACA
CAAAGGCTACCAATTGGAAAGAATTTCTTAAAGAGATTGATGAGAAGGGC
TTAGATGATGATGATCTAATTATTGGTCTTAAAGGAAAGGAGAGGGAACT
GAAGTTGGCAGGTAGATTTTTCTCCCTAATGTCTTGGAAATTGCGAGAAT
ACTTTGTAATTACCGAATATTTGATAAAGACTCATTTCGTCCCTATGTTT
AAAGGCCTGACAATGGCGGACGATCTAACTGCAGTCATTAAAAAGATGTT
AGATTCCTCATCCGGCCAAGGATTGAAGTCATATGAGGCAATTTGCATAG
CCAATCACATTGATTACGAAAAATGGAATAACCACCAAAGGAAGTTATCA
AACGGCCCAGTGTTCCGAGTTATGGGCCAGTTCTTAGGTTATCCATCCTT
AATCGAGAGAACTCATGAATTTTTTGAGAAAAGTCTTATATACTACAATG
GAAGACCAGACTTGATGCGTGTTCACAACAACACACTGATCAATTCAACC
TCCCAACGAGTTTGTTGGCAAGGACAAGAGGGTGGACTGGAAGGTCTACG
GCAAAAAGGATGGAGTATCCTCAATCTACTGGTTATTCAAAGAGAGGCTA
AAATCAGAAACACTGCTGTCAAAGTCTTGGCACAAGGTGATAATCAAGTT
ATTTGCACACAGTATAAAACGAAGAAATCGAGAAACGTTGTAGAATTACA
GGGTGCTCTCAATCAAATGGTTTCTAATAATGAGAAAATTATGACTGCAA
TCAAAATAGGGACAGGGAAGTTAGGACTTTTGATAAATGACGATGAGACT
ATGCAATCTGCAGATTACTTGAATTATGGAAAAATACCGATTTTCCGTGG
AGTGATTAGAGGGTTAGAGACCAAGAGATGGTCACGAGTGACTTGTGTCA
CCAATGACCAAATACCCACTTGTGCTAATATAATGAGCTCAGTTTCCACA
AATGCTCTCACCGTAGCTCATTTTGCTGAGAACCCAATCAATGCCATGAT
ACAGTACAATTATTTTGGGACATTTGCTAGACTCTTGTTGATGATGCATG
ATCCTGCTCTTCGTCAATCATTGTATGAAGTTCAAGATAAGATACCGGGC
TTGCACAGTTCTACTTTCAAATACGCCATGTTGTATTTGGACCCTTCCAT
TGGAGGAGTGTCGGGCATGTCTTTGTCCAGGTTTTTGATTAGAGCCTTCC
CAGATCCCGTAACAGAAAGTCTCTCATTCTGGAGATTCATCCATGTACAT
GCTCGAAGTGAGCATCTGAAGGAGATGAGTGCAGTATTTGGAAACCCCGA
G

FIG. 2E

FRAGMENT E (2664)
CCCGAGATAGCCAAGTTcCGAATAACTCACATAGACAAGCTAGTAGAAGA
TCCAACCTCTCTGAACATCGCTATGGGAATGAGTCCAGCGAACTTGTTAA
AGACTGAGGTTAAAAAATGCTTAATCGAATCAAGACAAACCATCAGGAAC
CAGGTGATTAAGGATGCAACCATATATTTGTATCATGAAGAGGATCGGCT
CAGAAGTTTCTTATGGTCAATAAATCCTCTGTTCCCTAGATTTTTAAGTG
AATTCAAATCAGGCACTTTTTTGGGAGTCGCAGACGGGCTCATCAGTCTA
TTTCAAAATTCTCGTACTATTCGGAACTCCTTTAAGAAAAGTATCATAG
GGAATTGGATGATTTGATTGTGAGGAGTGAGGTATCCTCTTTGACACATT
TAGGGAAACTTCATTTGAGAAGGGGATCATGTAAAATGTGGACATGTTCA
GCTACTCATGCTGACACATTAAGATACAAATCCTGGGGCCGTACAGTTAT
TGGGACAACTGTACCCCATCCATTAGAAATGTTGGGTCCACAACATCGAA
AAGAGACTCCTTGTGCACCATGTAACACATCAGGGTTCAATTATGTTTCT
GTGCATTGTCCAGACGGGATCCATGACGTCTTTAGTTCACGGGGACCATT
GCCTGCTTATCTAGGGTCTAAAACATCTGAATCTACATCTATTTTGCAGC
CTTGGGAAAGGGAAAGCAAAGTCCCACTGATTAAAAGAGCTACACGTCTT
AGAGATGCTATCTCTTGGTTTGTTGAACCCGACTCTAAACTAGCAATGAC
TATACTTTCTAACATCCACTCTTTAACAGGCGAAGAATGGACCAAAAGGC
AGCATGGGTTCAAAAGAACAGGGTCTGCCCTTCATAGGTTTTCGACATCT
CGGATGAGCCATGGTGGGTTCGCATCTCAGAGCACTGCAGCATTGACCAG
GTTGATGGCAACTACAGACACCATGAGGGATCTGGGAGATCAGAATTTCG
ACTTTTTATTCCAAGCAACGTTGCTCTATGCTCAAATTACCACCACTGTT
GCAAGAGACGGATGGATCACCAGTTGTACAGATCATTATCATATTGCCTG
TAAGTCCTGTTTGAGACCCATAGAAGAGATCACCCTGGACTCAAGTATGG
ACTACACGCCCCAGATGTATCCCATGTGCTGAAGACATGGAGGAATGGG
GAAGGTTCGTGGGGACAAGAGATAAAACAGATCTATCCTTTAGAAGGGAA
TTGGAAGAATTTAGCACCTGCTGAGCAATCCTATCAAGTCGGCAGATGTA
TAGGTTTTCTATATGGAGACTTGGCGTATAGAAAATCTACTCATGCCGAG
GACAGTTCTCTATTTCCTCTATCTATACAAGGTCGTATTAGAGGTCGAGG
TTTCTTAAAAGGGTTGCTAGACGGATTAATGAGAGCAAGTTGCTGCCAAG
TAATACACCGGAGAAGTCTGGCTCATTTGAAGAGGCCGGCCAACGCAGTG
TACGGAGGTTTGATTTACTTGATTGATAAATTGAGTGTATCACCTCCATT
CCTTTCTCTTACTAGATCAGGACCTATTAGAGACGAATTAGAAACGATTC
CCCACAAGATCCCAACCTCCTATCCGACAAGCAACCGTGATATGGGGGTG
ATTGTCAGAAATTACTTCAAATACCAATGCCGTCTAATTGAAAAGGGAAA
ATACAGATCACATTATTCACAATTATGGTTATTCTCAGATGTCTTATCCA
TAGACTTCATTGGACCATTCTCTATTTCCACCACCCTCTTGCAAATCCTA
TACAAGCCATTTTTATCTGGGAAAGATAAGAATGAGTTGAGAGAGCTGGC
AAATCTTTCTTCATTGCTAAGATCAGGAGAGGGGTGGGAAGACATACATG
TGAAATTCTTCACCAAGGACATATTATTGTGTCCAGAGGAAATCAGACAT
GCTTGCAAGTTCGGGATTGCTAAGGATAATAATAAAGACATGAGCTATCC
CCCTTGGGGAAGGGAATCCAGAGGGACAATTACAACAATCCCTGTTTATT
ATACGACCACCCCTTACCCAAAGATGCTAGAGATGCCTCCAAGAATCCAA
AATCCCCTGCTGTCCGGAATCAGGTTGGGCCAATTACCAACTGGCGCTCA
TTATAAAATTCGGAGTATATTACATGGAATGGGAATCCATTACAGGGACT
TCTTGAGTTGTGGAGACGGCTCCGGAGGGATGACTGCTGCATTACTACGA
GAAAATGTGCATAGCAGAGGAATATTCAATAGTCTGTTAGAATTATCAGG
GTCAGTCATGCGAGGCGCCTCTCCTGAGCCCCCAGTGCCCTAGAAACTT
TAGGAGGAGATAAATCGAGATGTGTAAATGGTGAAACATGTTGGGAATAT
CCATCTGACTTATGTGACCCAAGGACTTGGGACTATTTCCTCCGACTCAA
AGCAGGCTTGGGGCTTCAAATTGATTTAATTGTAATGGATATGGAAGTTC
GGGATTCTTCTACTAGCCTGAAAATTGAGACGAATGTTAGAAATTATGTG
CACCGGATTTTGGATGAGCAAGGAGTTTTAATCTACAAGACTTATGGAAC
ATATATTTGTGAGAGCGAAAAGAATGCAGTAACAATCCTTGGTCCCATGT
TCAAGACGGTCGAC

FIG. 2F

FRAGMENT F (930)

```
GTCGACTTAGTTCAAACAGAATTTAGTAGTTCTCAAACGTCTGAAGTATA
TATGGTATGTAAAGGTTTGAAGAAATTAATCGATGAACCCAATCCCGATT
GGTCTTCCATCAATGAATCCTGGAAAAACCTGTACGCATTCCAGTCATCA
GAACAGGAATTTGCCAGAGCAAAGAAGGTTAGTACATACTTTACCTTGAC
AGGTATTCCCTCCCAATTCATTCCTGATCCTTTTGTAAACATTGAGACTA
TGCTACAAATATTCGGAGTACCCACGGGTGTGTCTCATGCGGCTGCCTTA
AAATCATCTGATAGACCTGCAGATTTATTGACCATTAGCCTTTTTTATAT
GGCGATTATATCGTATTATAACATCAATCATATCAGAGTAGGACCGATAC
CTCCGAACCCCCCATCAGATGGAATTGCACAAAATGTGGGGATCGCTATA
ACTGGTATAAGCTTTTGGCTGAGTTTGATGGAGAAAGACATTCCACTATA
TCAACAGTGTTTAGCAGTTATCCAGCAATCATTCCCGATTAGGTGGGAGG
CTGTTTCAGTAAAAGGAGGATACAAGCAGAAGTGGAGTACTAGAGGTGAT
GGGCTCCCAAAAGATACCCGAATTTCAGACTCCTTGGCCCCAATCGGGAA
CTGGATCAGATCTCTGGAATTGGTCCGAAACCAAGTTCGTCTAAATCCAT
TCAATGAGATCTTGTTCAATCAGCTATGTCGTACAGTGGATAATCATTTG
AAATGGTCAAATTTGCGAAaAAACACAGGAATGATTGAATGGATCAATAG
ACGAATTTCAAAAGAAGACCGGTCTATACTGATGTTGAAGAGTGACCTAC
ACGAGGAAAACTCTTGGAGAGATTAAaaaatcatgaggagactccaaact
Ttaagtatgaaaaaactttgatccttaag
```

```
6001 TAAAGTCAT CTTAAGAAA ATACATGGCC TACAGCTGCT CAAGTTCAAG ATTTTGGAGA TAAATGGCAT GAACTTCCGC TGATTAAATG TTTTGAAATA 6100
6101 CCCGACTTAC TAGACCCATC GATAATATAC TCTGACAAAA GTCATTCAAT GAATAGGTCA GAGGTGTTGA AACATGTCCG AATGAATCCG AACACTCCTA 6200
6201 TCCCTACTAA AAAGGTGTTG CAGACTATGT TGGACACAAA GGCTACCAAT TGGAAAGAAT TTCTTAAAGA GATTGATGAG AAGGGCTTAG ATGATGATGA 6300
6301 TCTAATTATT GGTCTTAAAG GAAAGGAGAG GGAACTGAAG TTGGCAGGTA GATTTTTCTC CCTAATGTCT TGGAAATTGC GAGAATACTT TGTAATTACC 6400
6401 GAATATATTGA TAAAGACTCA TTTCGTCCCT ATGTTTAAAG GCCTGACAAT GGCGGACGAT TCAACTGCAG TCATTAAAAA GATGTTAGAT TCCTCATCCG 6500
6501 GCCAAGGATT GAAGTCATAT GAGGCAATTT GCATAGCCAA TCACATTGAT TACGAAAAAT GGAATAACCA CCAAAGGAAG TTATCAAACG GCCCAGTGTT 6600
6601 CCCGGAGTTATG GGCCAGTTCT TAGGTTATCC ATCCTTAATC GAGAGAACTC ATGAATTTTT TGAGAAAAGT CTTATATACT ACCAATGGAAG ACCAGACTTG 6700
6701 ATGGGAGTTC ACAACAACAC ACTGATCAAT TCAACCTCCC AACGAGTTTG TTGGCAAGGA CAAGAGGGTG GACTGGAAGG TCTACGGCAG AAAGGATGGA 6800
6801 GTATCCTCAA TCTACTGGTT ATTCAAAGAG AGGCTAAAAT CAGAAAACACT GCTGTCAAAG TCTTGGCACA AGTGATAAT CAAGTTATTT GCACACAGTA 6900
6901 TAAACGAAG AAATCGAGAA ACCTTGTAGA ATTACAGGGT GCTCTCAATC AAATGGTTTC TAATAATAG TAACTTTATGA CTGCAATCAA AATAGGGACA 7000
7001 GGGAAGTTAG GACTTTTGAT AAATGACGAT GAGACTATGC AATCTGCAGA TTACTTTGAAT TATGGAAAAA TACCGATTTT CCGTGGAGTG ATTAGAGGGT 7100
7101 TAGAGACCAA GAGATGGTCA CGAGTGACTT GTGTCACGAA TGACCAAATA CCCACTGTG CTAATATAAT GAGCTCAGTT CTCTCACCGT 7200
7201 AGCTCATTTT GCTGAGAACC CAATCAATGC CATGATAGAG CTTGGGACATT TTGGACACTC TGCTAGACTC TTGTTGATGA TGCATGATCC TGCTCTTCGT 7300
7301 CAATCATTGT GTATCATGAA GAGGATCGCA TCAGAAGTTCA AGATAAGATA CCCGGGCTTGC ACAGTTCTAC TTTCAAATAC GCCCATGTTGT ATTTGGACCC GGAGTGTCGG 7400
7401 GCATGTCTTT GTCCAGGTTT TTGATTAGAG CCCTTCCCAGA TCCCGTAACA GAAAGTCTCT CATTCTGGAG ATTCATCCAT GTACATGCTC GAAGTGAGCA 7500
7501 TCTGAAGGAG ATGAGTGCAG TATTTGGAAA CCCCCAGATA GCCAAGTTGC GAATAACTCA CATAGACAAG CTAGTAGACAAG ATCCAACCTC TCTGAACATC 7600
7601 GCTATGGGAA TGATCCGAGC GAACTTGTTA AAGACTGAGG TTAAAAATG CTTAATCGAA TCAAGACAAA CCATCAGGAA CCGGTGATT AAGGATGCAA 7700
7701 CCATATATTT GTATCATGAA GAGGATCGGC TCAGAAGTTT CTTATGGTCA ATAAATCCTC TGTTCCCTAG ATTTTTAAGT GAATTCAAAT CAGGCACTTT 7800
7801 TTTGGAGTC GCAGAACGGC TCATCAGTCT ATTTCAAAAT TCTCGTACTA TTCGAACTC CTTTAAGAA AAGTATCATA GGGAATTCATA TGATTGATT 7900
7901 GTGAGGAGTG AGGTATCCTC TTTGACACAT TAAGGAAAC TTCATTTGAG AAGGGGATCA TGTAAAATGT GGACATGTTC AGTACTCAT GCTGACACAT 8000
8001 TAAGAGACAA ATCCTGGGGC CGTACAGTTA TGGGACGAAC TGTACCCCAT CCATTAGAAA TGTTGGGTCC ACAACATCGA AAAGAGACTC CTTGTGCACC 8100
```

Aval

FIG. 3E

```
8101 ATGTAACACA TCAAGGTTCA ATTATGTTTC TGTCCATTGT CCAAGACGGGA TCCATGACGT CTTTAGTTCA CGGGGACCAT TGCCTGCTTA TCTAGGGTCT 8200
8201 AAACATCTG AATCTACATC TATTTGCAG CCTTGGGAAA CGGAAAGCAA AGTCCCACTG ATTAAAGAG CTACACGTCT TAGAGAATGT ATCTCTTGGT 8300
8301 TTGTTGAACC CGACTCTAAA CTAGCAATGA CTATACTTTC TAACATCCAC TCTTTAACAG GCGAAGAATG GACCAAAAGG CAGCAATGGGT TCAAAGAAAC 8400
8401 AGGGTTCTGCC CTTCATAGGT TTTGACATC TCGATGAGC CATGGTGGGT TGGCATCTCA GAGCACTGCA GGTTGATGGC AACTACAGAC 8500
8501 ACCATGAGGG ATCCGGAGAA TCAGAAATTTC GACTTTTTAT TCCAAGCAAC GTTGCTCTAT GCTCAAATTA CCACCACTGT TGCCAAGAGAC GGATGGATCA 8600
8601 CCAGTTGTAC AGATCATTAT CATATTGCCT GTAAGTCCTG TTTGAGACCC ATAGAAGAGA TCACCCTGGA CTTCAAGTATG GACTACCGC CCCCAGATGT 8700
8701 ATCCCATGTG CTTGAAGATGG CGGAGAATGG GGAAGGTTCG TGGGGACAAG AGATAAAACA GATCTATCCT TTAGAAGGGA ATTGCAAGAA TTTAGCACCT 8800
8801 GCTGAGCAAT CCTATCAAGT ATAGGTTGCA GTTTCTTAAA AGGTTGCTA CTTGGCGTAT AGAAAAATCTA CTCATGCCGA GGACAGTTCT CTATTTCCTC 8900
8901 TATCTATACA AGGTCGTATT CGGACAGCAT GTTCGGAAGA GTCGGAGGT TTGATTTACT TGATTGATAA ATTGAGTGTA TCATCTCCAT TACTAGATCA 9000
9001 GGCTCATTTG AAGAGGCCGG CCAACGCAGT GTACGGAGGT TTGATTTACT TGATTGATAA ATTGAGTGTA TCATCTCCAT TACTAGATCA 9100
9101 AATACCAATG CCGTCTAATT GAAAAGGGAA AATACAGATC ACATTATTCA CAATTATGGT TATTTTCAGA TGTCTTATCC ATAGAGCTGG CAAATCTTTC TTCATTGCTA 9200
9201 CTCTATTTCC ACCACCCTGA ATACAAGCCA GTGAAATTCT TCACCAAGGA CATATATTTG TGTTCAGAGG GAATGAGTTG AGAGAGCTTG TCGGGATTG 9300
9301 AGATCAGGAG AGGGGTGGGA AGACATACAT CCCCTTTGGG AAGGAAATCC AGAGGGACAA TTACAACAAT CCTTTTTAT TATACGACCA CCCCTTACCC 9400
9401 CTAAAGATAA TAATAAAGAC ATGAGCTATC CCCCTTGGG AAGGAAATCC AGAGGGACAA TTACAACAAT CCTTTTTAT TATACGACCA CCCCTTACCC 9500
9501 AAGATGCTA GAGTGCCTC CAGGAATCCA TCAGTTGGG CCAATTACCA ACTGGCGCTC ATTATAAAT TGGAGTATA 9600
9601 TTACATGGAA TCGGAATCCA TTTCAGGGAC TTCTTGACTT GTGGACACGG CTCCGAGGG ATGACTGCTG CATTACTACG AGAAATGTG CATTACACAG 9700
9701 GAATATTCAA TAGTCTGTTA GAATTATCGG GTTAGTCAT GCGAGGCGCC TCTCCTGAGC CCCCAGTGC CCTAGAAACT TTAGGAGGAG ATAAATGAG 9800
9801 ATGTGTAAAT GGTGGAATA GTTGGGAATA TCCATCGAC TTATGTGACC CAAGACTTTG GGACTATTTC CTCGACTCA AAGCAGGTTT GGGGCTTCAA 9900
9901 ATTCGATTAA ATTTATGGA TATGGAAGTT CGGGATTCTT CTACTAGCCT CGGGATTCGA ACGAATGTTA GAAATTATGT GCACCGATT TTGGATGAGC 10100
10101 AAGGAGTTTT AATCTACAAG CATATATTTG TGAGAGCGAA AAGAAATGCAG TAACAATCCT TGGTCCCATG TTCAAGACGG TTGACTTAGT 10200
``` sali

VESICULAR STOMATITIS VIRUS AND VIRUS RESCUE SYSTEM

INCORPORATION BY REFERENCE

This application is a continuation of U.S. application Ser. No. 13/623,437 filed Sep. 20, 2012 and claims priority to U.S. provisional patent application Ser. No. 61/537,497 filed Sep. 21, 2011. Reference is made to U.S. patent application Ser. No. 12/708,940 filed Feb. 19, 2010.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted in ASCII format and is hereby incorporated by reference in its entirety. Said ASCII copy, created on Nov. 19, 2012, is named 43094012.txt and is 82,769 bytes in size.

FIELD OF THE INVENTION

The present invention relates to a novel vesicular stomatitis virus for use in prophylactic and therapeutic vaccines.

BACKGROUND OF THE INVENTION

Vesicular stomatitis virus (VSV) is a member of the Rhabdoviridae family of enveloped viruses that contain a single-stranded, nonsegmented, negative-sense RNA genome. The VSV genome is composed of 5 genes arranged sequentially 3'-N-P-M-G-L-5', which each encode a polypeptide found in mature virions (Rose et al. 2001. Rhabdoviridae: the viruses and their replication, p. 1221-1244. In D. M. Knipe and P. M. Howley (ed.), Fields Virology, vol. 1. Lippincott, Williams and Wilkins, Philadelphia). The virus naturally infects livestock, but is known to infect humans producing mild illness or no symptoms of infection (Clarke et al. 2006. Springer seminars in immunopathology 28:239-253 and Letchworth et al. 1999. Vet J 157:239-260).

VSV is an important technology platform. It is a promising human vaccine vector candidate for a variety of reasons, notably, i) as mentioned above, it does not cause serious disease in humans; ii) genetic systems have been developed for producing recombinant viruses (Conzelmann. 2004. Curr Top Microbiol Immunol 283:1-41); iii) it can be modified to express foreign proteins; iv) it expresses foreign proteins abundantly; v) it elicits immune responses in infected humans (Reif et al. 1987. Am J Trop Med Hyg 36:177-182); and vi) it has been safely tested as a vaccine vector in many animal models including nonhuman primates (Clarke et al. 2006. Springer seminars in immunopathology 28:239-253).

There remains a need to express immunogens in recombinant vaccines. To do so, it is advantageous to have a vector that is genetically stable, easily modified, and efficiently propagated.

Citation or identification of any document in this application is not an admission that such document is available as prior art to the present application.

SUMMARY OF THE INVENTION

The invention stems, in part, from Applicants wishing to design a vector with a clearly defined and documented lineage that was specifically modified without altering amino acid coding or the function of cis-acting sequences to facilitate subsequent VSV vector construction. It was also important and practical to start with a VSV isolate adapted for propagation in primate epithelial cell lines (rather than commonly-used BHK fibroblastic cells) to promote greater genetic stability during VSV vector production in Vero cells used for vaccine manufacturing. Because Applicants' vaccine development plans included construction of highly modified VSV vectors that Applicants anticipated to be difficult to rescue, Applicants designed a cloning plasmid that included strategic modifications to increase the productivity of Applicants' recombinant virus rescue system.

The present invention relates to a vesicular stomatitis virus (VSV) genomic clone which may comprise: (a) a VSV genome encoding and expressing a nucleocapsid, phosphoprotein, matrix, glycoprotein and large protein, wherein the VSV genome may comprise nucleotide substitutions and amino acid coding changes to improve replicative fitness and genetic stability, (b) a cloning vector, (c) an extended T7 promoter, (d) a hammerhead ribozyme, (e) a hepatitis delta virus ribozyme and T7 terminator, (f) unique restriction endonuclease cleavage sites in a VSV genomic sequence and/or (g) a leader and a trailer that are cis-acting sequences controlling mRNA synthesis and replication.

In one embodiment, the cloning vector may be pSP72 (Genbank X65332.2). In another embodiment, the extended T7 promoter may be PT7-g10 (Lopez et al. 1997. Journal of molecular biology 269:41-51, the disclosure of which is incorporated by reference). RNA polymerase T7 functions first as a DNA binding protein that recognizes a specific DNA sequence and subsequently transitions its activity into an elongating RNA polymerase. The nature of the nucleotide sequence of the region initially transcribed by the polymerase plays a role in the transition from DNA binding protein to an elongating polymerase complex. The transcribed region in the PT7-g10 promoter may include nucleotide sequences that promote more efficient transition from DNA binding protein to elonagating RNA polymerase. (Temiakov D, Mentesana P E, Ma K, Mustaev A, Borukhov S, McAllister W T. The specificity loop of T7 RNA polymerase interacts first with the promoter and then with the elongating transcript, suggesting a mechanism for promoter clearance. Proc Natl Acad Sci USA. 2000 Dec. 19; 97 (26):14109-14, the disclosure of which is incorporated by reference).

In another embodiment, the unique restriction endonuclease cleavage sites may be 1367 NheI, 2194 SpeI, 2194 BstBI, 4687 PacI, 7532 AvaI, 10190 SalI and 11164 AflII. In yet another embodiment, the VSV genomic clones may be depicted in FIG. 1. In another embodiment, SphI and Xho1 may be added for cloning into position 1 between the leader and N gene junction of the VSV genomic clones depicted in FIG. 1.

The nucleotide substitutions in the VSV genome may be selected from the group consisting of: 1371 CA>GC (NheI), after 2195 insert TAG (SpeI) (all genome numbers subsequent to this insertion have been adjusted to include +3 bp), 3036 G>T improves match to consensus transcription stop signal, 3853 X>A (an ambiguity in Genbank file EF197793.1), 4691 T>A to generate PacI, 7546 C>A silent change in L coding sequence eliminates a BstBI site. Additionally, amino acids substitutions may be introduced to increase match with a VSV consensus using nucleotide substitutions selected from 1960 TAC>TCC to change Y>S, 3247 GTA>ATA to change V>I, 3729 AAG>GAG to change K>E, 4191 GTA>GAA to change V>E, 4386 GGT>GAT to change G>D, 4491 ACC>ATC to change T>I, 5339 ATT>CTT to change I>L, 5834 ACT>GCT to change T>A and/or 10959 AGA>AAA to change R>K, wherein the nucleotide position is according to GenBank Accession Number EF197793. The nucleotide substitutions in the VSV genome (wherein the nucleotide position is according to GenBank Accession Number EF197793) may be selected from the group consisting of:

increase the efficiency of synthesis and processing of full-length VSV genomic RNA in transfected cells.

In one embodiment, the T7 RNA polymerase promoter may be a minimal functional sequence designed to initiate transcription very close to or precisely at the 5' terminus of the genomic clone. Advantageously, the T7 promoter may be a T7 promoter sequence that enhances formation of stable initiation and elongation complexes and a hammerhead ribozyme sequence at the 5' terminus that catalyzes removal of extra nucleotides restoring the authentic 5' terminus of the genomic transcript.

In another embodiment, the plasmids used to support virus rescue encoding VSV nucleocapsid, phosphoprotein, matrix, glycoprotein and large protein may be optimized to improve expression of the trans-acting proteins to initiate virus rescue. Advantageously, the optimization is codon

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT > GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

The VSV genomic clone may comprise the nucleotide sequences of the VSV genome encoding and expressing a nucleocapsid, phosphoprotein, matrix, glycoprotein and large protein may be selected from the group consisting of FIGS. 2B-2G. The VSV genomic clone may also comprise the nucleotide sequences of the VSV genome encoding and expressing a nucleocapsid, phosphoprotein, matrix, glycoprotein and large protein may be selected from the group consisting of FIGS. 3A-3G.

The present invention also relates to method for rescuing VSV, which may comprise combining a T7 RNA polymerase promoter and a hammerhead ribozyme sequence to optimization. In one embodiment, the gene optimization may comprise replacing a VSV nucleotide sequence with codons used by highly expressed mammalian genes. In another embodiment, the codon optimization may comprise eliminating potential RNA processing signals in the coding sequence that might direct unwanted RNA splicing or cleavage/polyadenylation reaction, wherein the eliminating may comprise: (a) identifying potential splice site signals and remove by introducing synonymous codons and/or (b) scanning an insert for consensus cleavage/polyadenylation signals (AAUAAA) and introducing synonymous codons to disrupt the consensus cleavage/polyadenylation signals. In yet another embodiment, the gene optimization may comprise (a) adding a preferred translational start sequence (the Kozak sequence) and/or (b) adding a preferred translational stop codon. In still another embodiment, the gene optimization may comprise scanning a sequence for homopolymeric stretches of 5 nucleotides or more and interrupting the sequences by introducing synonymous codons. In another embodiment, the gene optimization may comprise scanning a sequence for restriction endonuclease cleavage sites and eliminate any unwanted recognitions signals. In yet another embodiment, the gene optimization may comprise confirming that a modified sequence translates into the expected amino acid sequence.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2B depicts a sequence of genome fragment VSV-A/G (1489 bp) (SEQ ID NO: 9).

FIG. 2C depicts a sequence of genome fragment B (1645 bp) (SEQ ID NO: 10).

FIG. 2D depicts a sequence of genome fragment C (1689 bp) (SEQ ID NO: 11).

FIG. 2E depicts a sequence of genome fragment D (2851 bp) (SEQ ID NO: 12).

FIG. 2F depicts a sequence of genome fragment E (2664) (SEQ ID NO: 13).

FIG. 2G depicts a sequence of genome fragment F (930) (SEQ ID NO: 14).

FIG. 3A depicts a schematic VSV annotated rVSV genomic cDNA and mRNA transcriptional control and processing signals. (SEQ ID NOS 15-16, respectively, in order of appearance).

FIGS. 3B-3G depict a sequence of the VSV (SEQ ID NO: 17) of FIG. 3A.

DETAILED DESCRIPTION

Figure 1:
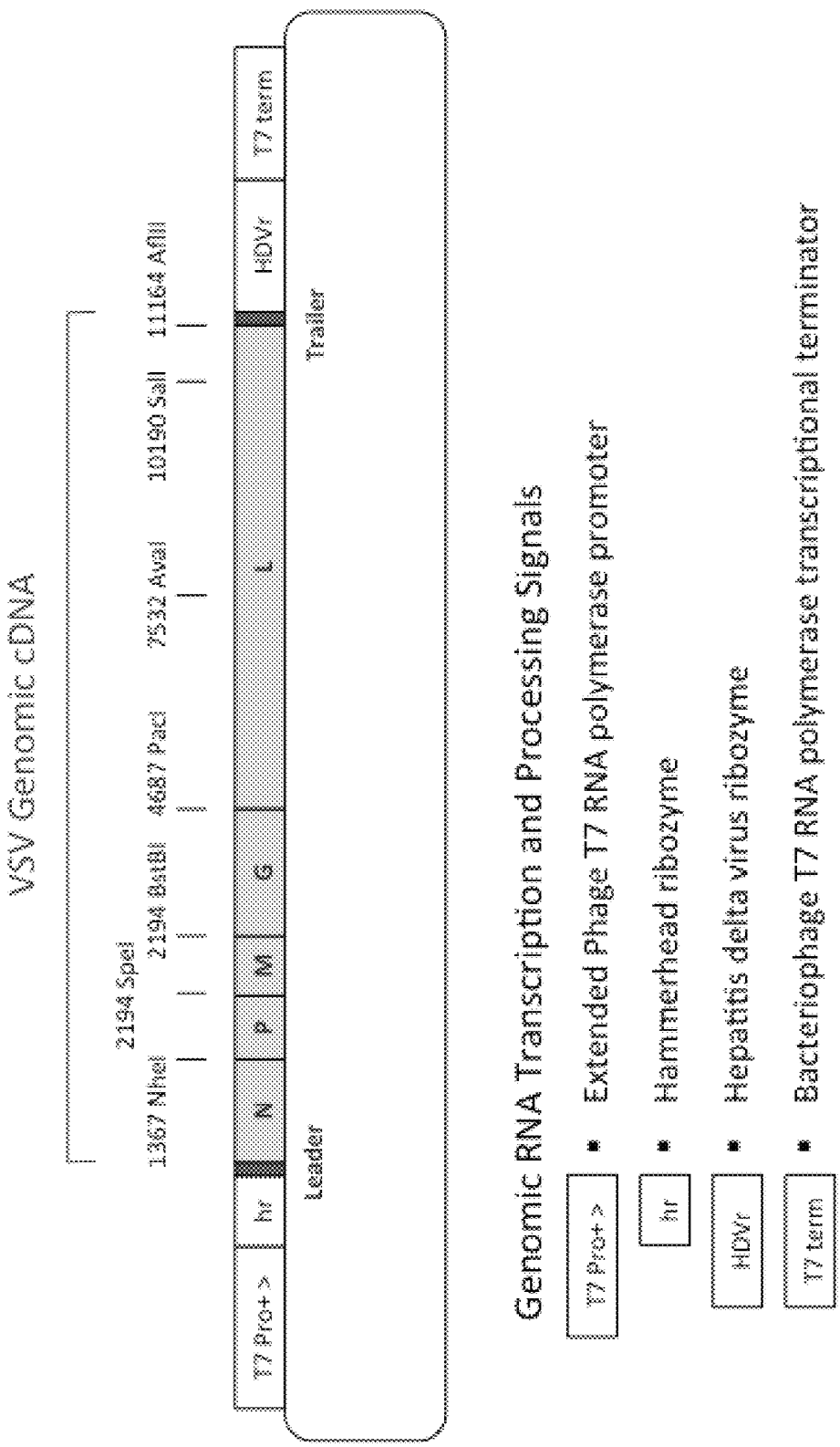
FIG. 1 depicts a schematic structure of a VSV genomic clone of the invention.

Applicants used VSV to develop several types of HIV vaccine candidate including VSV-SIV and VSV-HIV chimeric viruses in which the natural VSV attachment protein (G) is functionally replaced with SIV/HIV Env and and EnvG hybrids, vectors designed with Env epitopes grafted into VSV G and vectors designed to display a variety of Env immunogens as transmembrane proteins on the surface of VSV particles and infected cells.

Applicants used VSV to develop technology platforms for antibody-based screening and selection procedures that will allow Applicants to evolve novel Env immunogens. These methods take advantage of the fact that VSV evolves rapidly when selective pressure is applied (Novella. 2003. Curr Opin Microbiol 6:399-405). Methods in development include a procedure that allows Applicants to select for Env mutants that bind most strongly with monoclonal antibodies, a method for rapidly producing mutants that escape neutralizing antibodies that bind HIV Env, and a method for generating live or inactivated VSV particles displaying Env.

All of the recombinant VSVs are based on a genomic DNA clone Applicants designed. Applicants decided to develop Applicants' own VSV vector for several reasons. First, Applicants wanted to begin Applicants' vaccine development program with a vector that has a clearly defined and documented lineage. Second, Applicants planned to introduce a limited number of strategic nucleotide changes into the genome that would facilitate subsequent VSV vector construction without altering amino acid coding or the function of cis-acting sequences. Third, it was important and practical to start with a VSV isolate adapted for propagation in primate epithelial cell lines (rather than commonly-used BHK fibroblastic cells) to promote greater genetic stability during VSV vector production in Vero cells used for vaccine manufacturing. Finally, because Applicants' vaccine development plans included construction of highly modified rVSV vectors that Applicants anticipated to be difficult to rescue, Applicants designed a cloning plasmid that included strategic modifications to increase the productivity of Applicants' rescue system.

Applicants could have used the VSV vector background developed in 1995 at Yale University (Lawson et al. 1995. Proceedings of the National Academy of Sciences of the United States of America 92:4477-4481) as Applicants' starting material. Applicants decided against this option because the Yale vector is a hybrid constructed from sequences originating from multiple VSV isolates propagated under diverse laboratory conditions (it was constructed when molecular cloning was considerably more complex and costly), and for Applicants' purposes, the Yale clone also needed further modification to introduce unique restriction enzyme cleavage sites. Thus, Applicants found it simpler to engineer a vector fitting Applicants' needs by assembling synthetic DNA fragments based on a virus genomic sequence described in a manuscript by Remold and colleagues (Remold et al. 2008. Mol Biol Evol 25:1138-1147). In the end, Applicants' vector nucleotide sequence differs from circulating wild-type viruses (VSV Indiana) and the Yale molecular clone by about 1%.

To construct Applicants' VSV genomic clone (FIG. 1), Applicants started with the sequence (Genbank Accession EF197793) of a VSV isolate (Mudd Summers Strain, Indiana Serotype) adapted to growth in human epithelial cell lines (Remold et al. 2008. Mol Biol Evol 25:1138-1147). Applicants modified EF197793 nucleotide sequence to create unique restriction endonuclease cleavage sites (FIG. 1 and Table 1) that would facilitate subsequent genetic modification, and Applicants also introduced a number of nucleotide substitutions and amino acid coding changes that Applicants anticipated would improve the replicative fitness and genetic stability of Applicants' recombinant vector based on analysis of consensus sequences generated by aligning the genomes of lab-adapted and circulating wild-type viruses. The modified version of the EF197793 sequence (rEF197793 in Table 1) was then used as a template to have 6 DNA fragments synthesized, which Applicants subsequently assembled into the recombinant full-length genomic clone (FIGS. 2A-2G). An annotated modified VSV genomic sequence is included in FIGS. 3A-3G.

Applicants also introduced improvements to the plasmid DNA cloning vector that enhanced Applicants' ability to rescue recombinant VSV vectors from transfected cells. Applicants did this because, as mentioned above, Applicants' vaccine development plans included construction of highly modified VSV vectors that Applicants anticipated would be difficult to rescue because Applicants are adding one or more foreign gene inserts and also introducing changes expected to decrease replicative fitness. Negative-strand RNA virus rescue from cloned DNAs is a multistep process that includes: 1) cotransfection of multiple plasmid DNAs including the plasmid DNA containing the VSV genomic cDNA, a plasmid encoding bacteriophage T7 RNA polymerase, and multiple plasmids expressing viral proteins (i.e. VSV N, P, M, G, and L) needed to initiate virus replication in transfected cells; 2) intracellular synthesis of a full-length genomic RNA by bacteriophage T7 RNA polymerase; 3) precise processing of the primary genomic transcript to produce requisite termini for replication; 4) de novo packaging of the genomic RNA by the viral nucleocapsid protein to generate a functional template for RNA replication; 5) and finally, initiation of RNA synthesis by the viral RNA-dependent RNA polymerase (Conzelmann. 2004. Curr Top Microbiol Immunol 283:1-41 and Neumann et al. 2002. J Gen Virol 83:2635-2662). The rescue process is relatively inefficient and at times it restricts the ability to rescue the desired recombinant, although incremental improvements (Ghanem et al. 2011. European Journal of cell biology, Inoue et al. J Virol Methods 107:229-236, Parks et al. 1999. J Virol 73:3560-3566, Witko et al. 2010. J Virol Methods 164:43-50 and Witko et al. 2006. J Virol Methods 135:91-101) in the rescue procedure have made it more efficient since it was first described (Schnell et al. 1994. Embo J 13:4195-4203). As described herein, to improve Applicants' VSV rescue system, Applicants used a novel combination of a more efficient T7 RNA polymerase promoter and a hammerhead ribozyme sequence to increase the efficiency of synthesis and processing of full-length VSV genomic RNA in transfected cells.

The T7 RNA polymerase promoter used in published virus rescue methods is a minimal functional sequence designed to initiate transcription very close to or precisely at the 5' terminus of the genomic clone (Lawson et al. 1995. Proceedings of the National Academy of Sciences of the United States of America 92:4477-4481, Radecke et al. 1995. The EMBO Journal 14:5773-5784 and Schnell et al. 1994. Embo J 13:4195-4203). Although this promoter design is effective for forming the 5' end of the genomic transcript, it is not the most efficient promoter for initiating productive RNA synthesis. Thus, to improve VSV rescue efficiency, Applicants developed a modified plasmid that uses a longer T7 promoter sequence known to enhance formation of stable initiation and elongation complexes (Lopez et al. 1997. Journal of molecular biology 269:41-51). Because the longer T7 promoter includes downstream transcribed bacteriophage sequences, extra nucleotides are added to the primary VSV genomic transcript. To remove these extra nucleotides, Applicants have incorporated a hammerhead ribozyme (Inoue et al. J Virol Methods 107: 229-236 and Ruffner et al. 1990. Biochemistry 29:10695-10702) sequence at the 5' that which catalyzes removal of extra nucleotides restoring the authentic 5' end of the genomic transcript.

Finally, the VSV rescue system Applicants developed uses protocols similar to those described before with modification (Witko et al. 2006. J Virol Methods 135:91-101). The most significant change is that Applicants have 'optimized' (Examples 3 and 4) Applicants' plasmids encoding N, P, M, G, and L and placed the optimized genes under control of the human cytomegalovirus promoter to improve expression of the trans-acting proteins needed to initiate virus rescue. This modification of the rescue system was suggested by results showing that codon optimization significantly enhances expression in transfected cells of plasmid-encoded viral G proteins from respiratory syncytial virus and VSV (Ternette et al. 2007. Virol J 4:51 and Witko et al. 2010. J Virol Methods 164:43-50).

The present invention also encompasses methods of producing or eliciting an immune response that may comprise administering to an animal, advantageously a mammal, any one of the herein disclosed recombinant VSV vectors.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule may be produced by digestion of whole antibody with the enzyme papain to yield an intact light chain and a portion of one heavy chain;

(ii) Fab', the fragment of an antibody molecule may be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that may be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and IN sequences of the invention may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms may be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323;

6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

Advantageously, the HIV epitope may be an Env precursor or gp160 epitope. The Env precursor or gp160 epitope may be recognized by antibodies PG9, PG16, 2G12, b12, 2F5, 4E10, Z13, or other broad potent neutralizing antibodies.

In another embodiment, HN, or immunogenic fragments thereof, may be utilized as the HIV epitope. For example, the HN nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention may be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector may be used depending on the application. For example, plasmids, viral vectors, bacterial vectors, protozoan vectors, insect vectors, baculovirus expression vectors, yeast vectors, mammalian cell vectors, and the like, may be used. Suitable vectors may be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors.

The present invention relates to recombinant vesicular stomatitis (VSV) vectors, however, other vectors may be contemplated in other embodiments of the invention such as, but not limited to, prime boost administration which may comprise administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

The VSVs of U.S. Pat. Nos. 7,468,274; 7,419,829; 7,419,674; 7,344,838; 7,332,316; 7,329,807; 7,323,337; 7,259,015; 7,244,818; 7,226,786; 7,211,247; 7,202,079; 7,198,793; 7,198,784; 7,153,510; 7,070,994; 6,969,598; 6,958,226; RE38,824; PPI5,957; 6,890,735; 6,887,377; 6,867,326; 6,867,036; 6,858,205; 6,835,568; 6,830,892; 6,818,209; 6,790,641; 6,787,520; 6,743,620; 6,740,764; 6,740,635; 6,740,320; 6,682,907; 6,673,784; 6,673,572; 6,669,936; 6,653,103; 6,607,912; 6,558,923; 6,555,107; 6,533,855; 6,531,123; 6,506,604; 6,500,623; 6,497,873; 6,489,142; 6,410,316; 6,410,313; 6,365,713; 6,348,312; 6,326,487; 6,312,682; 6,303,331; 6,277,633; 6,207,455; 6,200,811; 6,190,650; 6,171,862; 6,143,290; 6,133,027; 6,121,434; 6,103,462; 6,069,134; 6,054,127; 6,034,073; 5,969,211; 5,935,822; 5,888,727; 5,883,081; 5,876,727; 5,858,740; 5,843,723; 5,834,256; 5,817,491; 5,792,604; 5,789,229; 5,773,003; 5,763,406; 5,760,184; 5,750,396; 5,739,018; 5,698,446; 5,686,279; 5,670,354; 5,540,923; 5,512,421; 5,090,194; 4,939,176; 4,738,846; 4,622,292; 4,556,556 and 4,396,628 may be contemplated by the present invention.

The nucleotide sequences and vectors of the invention may be delivered to cells, for example if the aim is to express HIV-1 antigens in cells in order to produce and isolate the expressed proteins, such as from cells grown in culture. For expressing the antibodies and/or antigens in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens may be carried out in any suitable type of host cells, such as bacterial cells, yeast, insect cells, and mammalian cells. The antibodies and/or antigens of the invention may also be expressed including using in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition may also be formulated in the form of an oil-in-water emulsion. The oil-in-water emulsion may be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers may be non-ionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant may be a mixture of emulsifier(s), micelle-forming agent, and oil such as that which is commercially available under the name Provax® (IDEC Pharmaceuticals, San Diego, Calif.).

The immunogenic compositions of the invention may contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK$(SO_4)_2$, AlNa$(SO_4)_2$, AlNH$(SO_4)_2$, silica, alum, Al$(OH)_3$, Ca3$(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71 (3): 538-44; Ahmad-Nejad, P. et al (2002) Eur. J. Immunol. 32 (7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20 (29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169 (7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22 (13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that may be used, especially with DNA vaccines, are cholera toxin, especially CTA1-DD/ISCOMs (see Mowat, A. M. et al (2001) J. Immunol. 167 (6): 3398-405), polyphosphazenes (Allcock, H. R. (1998) App. Organometallic Chem. 12 (10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD4OL (ADX40; see, for example, WO03/063899), and the CD1a ligand of natural killer cells (also known as CRONY or α-galactosyl ceramide; see Green, T. D. et al, (2003) J. Virol. 77 (3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which may be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions may be designed to introduce the nucleic acids or expression vectors to a desired site of action and release it at an appropriate and controllable rate. Methods of preparing controlled-release formulations are known in the art. For example, controlled release preparations may be produced by the use of polymers to complex or absorb the immunogen and/or immunogenic composition. A controlled-release formulation may be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention may be readily determined by those of skill in the art. For example, the dosage of the immunogens may vary depending on the route of administration and the size of the subject. Suitable doses may be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions may serve to provide protective immunity of a subject against HIV-1 infection or to prevent or attenuate the progression of AIDS in a subject already infected with HIV-1. When provided therapeutically, the immunogenic compositions may serve to ameliorate and treat AIDS symptoms and are advantageously used as soon after infection as possible, preferably before appearance of any symptoms of AIDS but may also be used at (or after) the onset of the disease symptoms.

The immunogenic compositions may be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes may be oral, intranasal or by any other suitable route. Delivery may also be accomplished via a mucosal surface such as the anal, vaginal or oral mucosa. Immunization schedules (or regimens) are well known for animals (including humans) and may be readily determined for the particular subject and immunogenic composition. Hence, the immunogens may be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response may also include administration of an adjuvant with the immunogens. In some instances, annual, biannual or other long interval (5-10 years) booster immunization may supplement the initial immunization protocol.

The present methods also include a variety of prime-boost regimens, for example DNA prime-VSV boost regimens. In these methods, one or more priming immunizations are followed by one or more boosting immunizations. The actual immunogenic composition may be the same or different for each immunization and the type of immunogenic composition (e.g., containing protein or expression vector), the route, and formulation of the immunogens may also be varied. For example, if an expression vector is used for the priming and boosting steps, it may either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen may also include VSV vectors that derive their G protein or G/Stem protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J Virol. 2000 December; 74 (23):10903-10). The VSV vectors used in these examples contain a G or G/Stem protein derived from the Indiana serotype of VSV. Vectors may also be constructed to express G or G/Stem molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus a prime may be delivered in the context of a G or G/Stem molecule that is from the Indiana serotype and the immune system may be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an VSV vector containing RNA encoding one or more of the epitopes of the invention, one or more times to a subject wherein the epitopes are expressed at a level sufficient to induce a specific immune response in the subject. Such immunizations may be repeated multiple times at time intervals of at least 2, 4 or 6 weeks (or more) in accordance with a desired immunization regime.

The immunogenic compositions of the invention may be administered alone, or may be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages may be determined taking into consideration such factors as the age, sex, weight, species and condition of the particular subject, and the route of administration.

When used in combination, the other HIV immunogens may be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which may be administered as a protein, on a plasmid (e.g., pTHr.HIVA) or in a viral vector (e.g., MVA. HIVA). Another such HIV immunogen is RENTA (described in PCT/US2004/037699), which may also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose may be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response may include an HIV-specific T-cell immune response or an HIV-specific B-cell immune response. Such immunizations may be done at intervals, preferably of at least 2-6 or more weeks.

It is to be understood and expected that variations in the principles of invention as described above may be made by one skilled in the art and it is intended that such modifications, changes, and substitutions are to be included within the scope of the present invention.

The invention will now be further described by way of the following non-limiting examples.

EXAMPLES

Example 1: Recombinant VSV Vector Construction

Structure of the IAVI VSV genomic clone as depicted in FIG. 1.

Features include:
1. The cloning vector is based on pSP72 (Genbank X65332.2).
2. The extended T7 promoter is PT7-g10 described by Lopez et al. (Lopez et al., 1997. Journal of molecular biology 269:41-51)
3. The hammerhead ribozyme was designed following the rules for constructing self-cleaving RNA sequences (Inoue et al. 2003. J Virol Methods 107:229-236 and Ruffner et al. 1990. Biochemistry 29:10695-10702).
4. The hepatitis delta virus ribozyme and T7 RNA polymerase terminator were used as described before for the measles virus rescue system (Radecke et al. 1995. The EMBO journal 14:5773-5784, 23 and Sidhu et al. 1995. Virology 208:800-807)
5. Unique restriction endonuclease cleavage sites in the recombinant VSV genome (red) are indicated above the genome map.
6. The Leader and Trailer are cis-acting sequences in the termini that control mRNA synthesis and replication.
7. The viral proteins N, nucleocapsid; P, phosphoprotein; M, matrix; G, glycoprotein; L, large protein.

Recombinant VSV Vector Construction

Indiana Serotype

Based on Genbank EF197793—modified as described below:

Nucleotide substitutions introduced to generate unique restriction sites or bring sequence closer to consensus
   1371 CA>GC (NheI)
   After 2195 insert TAG (SpeI) (all genome numbers below adjusted to include +3 bp introduced by this insertion)
   3036 G>T improves match to consensus transcription stop signal
   3853 X>A (X was an ambiguity in Genbank file)
   4691 T>A to generate PacI 7546 C>A silent change in L coding sequence eliminates a BstBI site
1960 TAC>TCC to change Y>S
3247 GTA>ATA to change V>I
3729 AAG>GAG to change K>E
4191 GTA>GAA to change V>E
4386 GGT>GAT to change G>D
4491 ACC>ATC to change T>I
5339 ATT>CTT to change I>L
5834 ACT>GCT to change T>A
10959 AGA>AAA to change R>K A VSV genome and cloning fragments are depicted in FIGS. 2A-G.

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT > GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

TABLE 1

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

```
Genbank X65332.2: Cloning vector pSP72
LOCUS       X65332                  2462 bp    DNA     circular SYN 25-JAN-2000
DEFINITION  Cloning vector pSP72.
ACCESSION   X65332
VERSION     X65332.2  GI:6759494
KEYWORDS    beta-lactamase; bla gene; cloning vector; multiple cloning site;
            promoter.
SOURCE      Cloning vector pSP72
  ORGANISM  Cloning vector pSP72
            other sequences; artificial sequences; vectors.
REFERENCE   1
  AUTHORS   Technical, Services.
  TITLE     Direct Submission
  JOURNAL   Submitted (23-MAR-1992) Technical Services, Promega Corporation,
            2800 Woods Hollow Road, Madison, Wi 53711-5399, USA
  REMARK    revised by [2]
REFERENCE   2
```

TABLE 1-continued

Modifications introduced into the VSV genomic sequence (Genbank accession EF197793) are listed. Note that Line 3 includes a 3

TABLE 1-continued

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

```
1141       atgcttaatc agtgaggcac ctatctcagc gatctgtcta tttcgttcat ccatagttgc
1201       ctgactcccc gtcgtgtaga taactacgat acgggagggc ttaccatctg gccccagtgc
1261       tgcaatgata ccgcgagacc cacgctcacc ggctccagat ttatcagcaa taaaccagcc
1321       agccggaagg gccgagcgca gaagtggtcc tgcaacttta tccgcctcca tccagtctat
1381       taattgttgc cgggaagcta gagtaagtag ttcgccagtt aatagtttgc gcaacgttgt
1441       tgccattgct acaggcatcg tggtgtcacg ctcgtcgttt ggtatggctt cattcagctc
1501       cggttcccaa cgatcaaggc gagttacatg atcccccatg ttgtgcaaaa aagcggttag
1561       ctccttcggt cctccgatcg ttgtcagaag taagttggcc gcagtgttat cactcatggt
1621       tatggcagca ctgcataatt ctcttactgt catgccatcc gtaagatgct tttctgtgac
1681       tggtgagtac tcaaccaagt cattctgaga atagtgtatg cggcgaccga gttgctcttg
1741       cccggcgtca atacgggata ataccgcgcc acatagcaga actttaaaag tgctcatcat
1801       tggaaaacgt tcttcgggge gaaaactctc aaggatctta ccgctgttga gatccagttc
1861       gatgtaaccc actcgtgcac ccaactgatc ttcagcatct tttactttca ccagcgtttc
1921       tgggtgagca aaaacaggaa ggcaaaatgc cgcaaaaaag ggaataaggg cgacacggaa
1981       atgttgaata ctcatactct tccttttca atattattga gcatttatc aggttattg
2041       tctcatgagc ggatacatat ttgaatgtat ttagaaaaat aaacaaatag gggttccgcg
2101       cacatttccc cgaaaagtgc cacctgacgt ctaagaaacc attattatca tgacattaac
2161       ctataaaaat aggcgtatca cgaggccctt tcgtctcgcg cgtttcggtg atgacggtga
2221       aaacctctga cacatgccagc tcccggagac ggtcacagct tgtctgtaag cggatgccgg
2281       gagcagacaa gcccgtcagg gcgcgtcagc gggtgttggc gggtgtcggg gctggcttaa
2341       ctatgcggca tcagagcaga ttgtactgag agtgcaccat atggacatat tgtcgttaga
2401       acgcggctac aattaataca taaccttatg tatcatacac atacgattta ggtgacacta
2461       ta//
```

Genbank EF197793: *Vesicular stomatitis Indiana virus, complete genome*
LOCUS       EF197793                11161 bp    cRNA     linear   VRL 15-APR-2007
DEFINITION  *Vesicular stomatitis Indiana* virus, complete genome.
ACCESSION   EF197793
VERSION     EF197793.1  GI:144678900
SOURCE      *Vesicular stomatitis Indiana* virus
ORGANISM    *Vesicular stomatitis Indiana* virus
            Viruses; ssRNA negative-strand viruses; *Mononegavirales*;
            *Rhabdoviridae*; *Dimarhabdovirus* supergroup; *Vesiculovirus*.
REFERENCE   1  (bases 1 to 11161)
AUTHORS     Remold,S.K., Rambaut,A. and Turner,P.T.
TITLE       Evolutionary genomics of host adaptation in *Vesicular stomatitis virus*
JOURNAL     Unpublished
REFERENCE   2  (bases 1 to 11161)
AUTHORS     Remold,S.K.
TITLE       Direct Submission
JOURNAL     Submitted (22-DEC-2006) Biology, University of Louisville, 139
            Life Sciences Building, Louisville, KY 40292, USA
FEATURES             Location/Qualifiers
     source          1..11161
                     /organism="*Vesicular stomatitis Indiana* virus"
                     /mol_type="viral cRNA"
                     /isolate="MARMC from S.F. Elena Lab, 2001"
                     /db_xref="taxon:11277"
                     /country="USA"
     gene            51..1376
                     /gene="N"
     CDS             64..1332
                     /gene="N"
                     /codon_start=1
                     /product="nucleoprotein"
                     /protein_id="ABP01780.1"
                     /db_xref="GI:144678901"

(SEQ ID NO: 3)
/translation="MSVIVKRIIDNIVIVPKLPANEDPVEYPADYFRKSKEIPLYINT
TKSLSDLRGYVYQGLKSGNVSIIHVNSYLYGALKDIRGKLDKDWSSEGINIGKAGDTI
GIFDLVSLKALDGVLPDGVSDASRTSADDKWLPLYLLGLYRVGRTQMPEYRKRLMDGL
TNQCKMINEQFEPLVPEGRDIFDVWGNDSNYTKIVAAVDMFEHMFKKHECASFRYGTI
VSRFKDCAALATFGHLCKITGMSTEDVTTWILNREVADEMVQMMLPGQEIDKADSYMP
YLIDFGLSSKSPYSSVKNPAFHFWGQLTALLLRSTRARNARQPDDIEYTSLTTAGLLY
AYAVGSSADLAQQFCVGDSKYTPDDSTGGLTTNAPPQGRDVVEWLGWFEDQNRKPTPD
MMQYAKRAVMSLQGLREKTIGKYAKSEFDK"

gene            1386..2199
                     /gene="P"

TABLE 1-continued

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

```
CDS             1396..2193
                /gene="P"
                /codon_start=
                /product="phosphoprotein"
                /protein_id="ABP01781.1"
                /db_xref="GI:144678902"
```
(SEQ ID NO: 4)

/translation="MDNLTKVREYLKSYSRLDQAVGEIDEIEAQRAEKSNYELFQEDG
VEEHTRPSYFQAADDSDTESEPEIEDNQGLYVPDPEAEQVEGFIQGPLDDYADEDVDV
VFTSDWKQPELESDEHGKTLRLTLPEGLSGEQKSQWLLTIKAVVQSAKHWNLAECTFE
ASGEGVIIKKRQITPDVYKVTPVMNTHPYQSEAVSDVWSLSKTSMTFQPKKASLQPLT
ISLDELFSSRGEFISVGGNGRMSHKEAILLGLRYKKLYNQARVKYSL"

```
gene            2209..3039
                /gene="M"
CDS             2250..2939
                /gene="M"
                /codon_start=1
                /product="matrix"
                /protein_id="ABP01782.1"
                /db_xref="GI:144678903"
```
(SEQ ID NO: 5)

/translation="MSSLKKILGLKGKGKKSKKLGIAPPPYEEDTNMEYAPSAPIDKS
YFGVDEMDTHDPNQLRYEKFFFTVKMTVRSNRPFRTYSDVAAAVSHWDHMYIGMAGKR
PFYKILAFLGSSNLKATPAVLADQGQPEYHAHCEGRAYLPHRMGKTPPMLNVPEHFRR
PFNIGLYKGTIELTMTIYDDESLEAAPMIWDHENSSKFSDFREKALMFGLIVEKKASG
AWVLDSVSHFK"

```
gene            3049..4713
                /gene="G"
CDS             3078..4613
                /gene="G"
                /codon_start=1
                /product="glycoprotein"
                /protein_id="ABP01783.1"
                /db_xref="GI:144678904"
```
(SEQ ID NO: 6)

/translation="MKCLLYLAFLFIGVNCKFTIVEPHNQKGNWKNVPSNYHYCPSSS
DLNWHNDLVGTALQVKMPKSHKAIQADGWMCHASKWVTTCDFRWYGPKYITHSIRSFT
PSVEQCKESIEQTKQGTWLNPGFPPQSCGYATVTDAEAAIVQVTPHHVLVDEYTGEWV
DSQFINGKCSNDICPTVHNSTTWHSDYKVKGLCDSNLISMDITFFSEDGELSSLGKKG
TGFRSNYFAYETGDKACKMQYCKHWGVRLPSGVWFEMADKXLFAAARFPECPEGSSIS
APSQTSVDVSLIQDVERILDYSLCQETWSKIRAGLPISPVDLSYLAPKNPGTGPVFTI
INGTLKYFETRYIRVDIAAPILSRMVGMISGTTTERVLWDDWAPYEDVEIGPNGVLRT
SSGYKFPLYMIGHGMLDSDLHLSSKAQVFEHPHIQDAASQLPDGETLFFGDTGLSKNP
IEFVEGWFSSWKSSIASFFFTIGLIIGLFLVLRVGIYLCIKLKHTKKRQIYTDIEMNR
LGK"

```
gene            4723..11095
                /gene="L"
CDS             4733..11062
                /gene="L"
                /codon_start=1
                /product="large protein"
                /protein_id="ABP01784.1"
                /db_xref="GI:144678905"
```
(SEQ ID NO: 7)

/translation="MEVHDFETDEFNDFNEDDYATREFLNPDERMTYLNHADYNLNSP
LISDDIDNLIRKFNSLPIPSMWDSKNWDGVLEMLISCQANPISTSQMHKWMGSWLMSD
NHDASQGYSFLHEVDKEAEITFDVVETFIRGWGNKPIEYIKKERWIDSFKILAYLCQK
FLDLHKLTLILNAVSEVELLNLARTFKGKVRRSSHGTNICRIRVPSLGPTFISEGWAY
FKKLDILMDRNFLLMVKDVIIGRMQTVLSMVCRIDNLFSEQDIFSLLNIYRIGDKIVE
RQGNFSYDLIKMVEPICNLKLMKLARESRPLVPQFPHFENHIKTSVDEGAKIDRGIRF
LHDQIMSVKIVDLTLVIYGSFRHWGHPFIDYYTGLEKLHSQVIMKKDIDVSYAKALAS
DLARIVLFQQFNDHKKWFVNGDLLPHDHPFKSHVKENTWPTAAQVQDFGDKWHELPLI
KCFEIPDLLDPSIIYSDKSHSMNRSEVLKHVRMNPNIPIPSKKVLQTMLDTKATNWKE
FLKEIDEKGLDDDDLIIGLKGKERELKLAGRFFSLMSWKLREYFVITEYLIKTHFVPM
FKGLIMADDLTAVIKKMLDSSSGQGLKSYEAICIANHIDYEKWNNHQRKLSNGPVERV
MGQFLGYPSLIERTHEFFEKSLIYYNGRPDLMRVHNNTLINSTSQRVCWQGQEGGLEG
LRQKGWSILNLLVIQREAKIRNTAVKVLAQGDNQVICTQYKIKKSRNVVELQGALNQM
```

TABLE 1-continued

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

```
VSNNEKIMTAIKIGIGKLGLLINDDETMQSADYLNYGKIPIFRGVIRGLETKRWSRVT
CVINDQIPTCANIMSSVSTNALTVAHFAENPINAMIQYNYFGTFARLLLMMHDPALRQ
SLYEVQDKIPGLHSSTFKYAMLYLDPSIGGVSGMSLSRFLIRAFPDPVTESLSFWRFI
HVHARSEHLKEMSAVFGNPEIAKFRITHIDKLVEDPISLNIAMGMSPANLLKTEVKKC
LIESRQTIRNQVIKDATIYLYHEEDRLRSFLWSINPLFPRFLSEFKSGTFLGVADGLI
SLFQNSRTIRNSFKKKYHRELDDLIVRSEVSSLTHLGKLHLRRGSCKMWTCSATHADT
LRYKSWGRIVIGTIVPHPLEMLGPQHRKETPCAPCNTSGFNYVSVHCPDGIHDVFSSR
GPLPAYLGSKTSESTSILQPWERESKVPLIKRATRLRDAISWFVEPDSKLAMTILSNI
HSLTGEEWTKRQHGFKRTGSALHRFSTSRMSHGGFASQSTAALTRLMATTDTMRDLGD
QNFDFLFQATLLYAQITTIVARDGWITSCIDHYHIACKSCLRPIEEITLDSSMDYIPP
DVSHVLKTWRNGEGSWGQEIKQIYPLEGNWKNLAPAEQSYQVGRCIGFLYGDLAYRKS
THAEDSSLFPLSIQGRIRGRGFLKGLLDGLMRASCCQVIHRRSLAHLKRPANAVYGGL
IYLIDKLSVSPPFLSLIRSGPIRDELETIPHKIPTSYPTSNRDMGVIVRNYFKYQCRL
IEKGKYRSHYSQLWLFSDVLSIDFIGPFSISTILLQILYKPFLSGKDKNELRELANLS
SLLRSGEGWEDIHVKFFIKDILLCPEEIRHACKFGIAKDNNKDMSYPPWGRESRGTIT
TIPVYYTTIPYPKMLEMPPRIQNPLLSGIRLGQLPTGAHYKIRSILHGMGIHYRDFLS
CGDGSGGMTAALLRENVHSRGIFNSLLELSGSVMRGASPEPPSALETLGGDKSRCVNG
ETCWEYPSDLCDPRTWDYFLRLKAGLGLQIDLIVMDMEVRDSSTSLKIETNVRNYVHR
ILDEQGVLIYKTYGTYICESEKNAVTILGPMFKIVDLVQTEFSSSQTSEVYMVCKGLK
KLIDEPNPDWSSINESWKNLYAFQSSEQEFARAKKVSTYFTLIGIPSQFIPDPFVNIE
TMLQIFGVPIGVSHAAALKSSDRPADLLTISLFYMAIISYYNINHIRVGPIPPNPPSD
GIAQNVGIAITGISFWLSLMEKDIPLYQQCLAVIQQSFPIRWEAVSVKGGYKQKWSTR
GDGLPKDTRISDSLAPIGNWIRSLELVRNQVRLNPFNEILFNQLCRIVDNHLKWSNLR
RNTGMIEWINRRISKEDRSILMLKSDLHEENSWRD"

ORIGIN
                                                                (SEQ ID NO: 8)
     1     acgaagacaa acaaaccatt attatcatta aaaggctcag gagaaacttt aacagtaatc
    61     aaaatgtctg ttacagtcaa gagaatcatt gacaacacag tcatagttcc aaaacttcct
   121     gcaaatgagg atccagtgga atacccggca gattacttca gaaaatcaaa ggagattcct
   181     ctttacatca atactacaaa aagtttgtca gatctaagag gatatgtcta ccaaggcctc
   241     aaatccggaa atgtatcaat catacatgtc aacagctact tgtatggagc attgaaggac
   301     atccggggta agttggataa agattggtca agtttcggaa taaacatcgg gaaggcaggg
   361     gatacaatcg gaatatttga ccttgtatcc ttgaaagccc tggacggtgt acttccagat
   421     ggagtatcgg atgcttccag aaccagcgca gatgacaaat ggttgccttt gtatctactt
   481     ggcttataca gagtgggcag aacacaaatg cctgaataca gaaaaaggct catggatggga
   541     ctgacaaatc aatgcaaaat gatcaatgaa cagtttgaac ctcttgtgcc agaaggtcgt
   601     gacattttg atgtgtgggg aaatgacagt aattacacaa aaattgtcgc tgcagtggac
   661     atgttcttcc acatgttcaa aaaacatgaa tgtgcctcgt tcagatacgg aactattgtt
   721     tccagattca aagattgtgc tgcattggca acatttggac acctctgcaa ataaccgga
   781     atgtctacag aagatgtgac gacctggatc ttgaaccgag aagttgcaga tgagatggtc
   841     caaatgatgc ttccaggcca agaaattgac aaggctgatt catacatgcc ttatttgatc
   901     gactttggat tgtcttctaa gtctccatat tcttccgtca aaaccctgc cttccacttc
   961     tgggggcaat tgacagctct tctgctcaga tccaccagag caaggaatgc ccgacagcct
  1021     gatgacattg agtatacatc tcttactaca gcaggtttgt tgtacgctta tgcagtagga
  1081     tcctctgctg acttggcaca acagtttgt gttggagata gcaaatacac tccagatgat
  1141     agtaccggag gattgacgac taatgcaccg ccacaaggca gagatgtggt cgaatggctc
  1201     ggatggtttg aagatcaaaa cagaaaaccg actcctgata tgatgcagta tgcgaaacga
  1261     gcagtcatgt cactgcaagg cctaagagag aagacaattg gcaagtatgc taagtcagag
  1321     tttgacaaat gacccctataa ttctcagatc acctattata tattatgcta catatgaaaa
  1381     aaactaacag atatcatgga taatctcaca aaagttcgtg agtatctcaa gtcctattct
  1441     cgtctagatc aggcggtagg agagatagat gagatcgaag cacaacgagc tgaaaagtcc
  1501     aattatgagt tgttccaaga ggacggagtg gaagagcata ctaggccctc ttattttcag
  1561     gcagcagatg attctgacac agaatctgaa ccagaaattg aagacaatca aggcttgtat
  1621     gtaccagatc cggaagctga gcaagttgaa ggctttatac aggggccttt agatgactat
  1681     gcagatgagg acgtggatgt tgtattcact tcggactgga aacacctga gcttgatcc
  1741     gacgagcatg gaaagacctt acggttgaca ttgccagagg gtttaagtgg agagcagaaa
  1801     tcccagtggc ttttgacgat taaagcagtc gttcaaagtg ccaaacactg gaatctggca
  1861     gagtgcacat tgaagcatc gggagaaggg gtcatcataa aaagcgcca gataactccg
  1921     gatgtatata aggtcactcc agtgatgaac acacatccgt accaatcaga gccgtatca
  1981     gatgttggt ctctctcaaa gacatccatg actttcaac ccaagaaagc aagttctcag
  2041     cctctcacca tatccttgga tgaattgttc tcatctagag gagaattcat ctctgtcgga
  2101     ggtaacggac gaatgtctca taaagaggcc atcctgctcg gtctgaggta caaaaagttg
  2161     tacaatcagg cgagagtcaa atattctctg tagactatga aaaaaagtaa cagatatcac
  2221     aatctaagtg ttatcccaat ccattcatca tgagttcctt aaagaagatt ctcggtctga
  2281     agggaaagg taagaaatct aagaaattag ggatcgcacc accccctta gaagaggaca
  2341     ctaacatgga gtatgctcag acgcgtccaa ttgacaaatc ctattttgga gttgacgaga
  2401     tggacactca tgatccgaat caattaagat atgagaaatt cttctttaca gtgaaaatga
  2461     cggttagatc taatcgtccg ttcagaacat actcagatgt ggcagccgct gtatcccatt
  2521     gggatcacat gtacatcgga atggcaggga acgtcccttc tacaagatc ttggctttt
  2581     tgggttcttc taatctaaag gccactccag cggtattggc agatcaaggt caaccagagt
  2641     atcatgctca ctgtgaaggc agggcttatt tgccacacag aatggggaag accctcgcca
```

TABLE 1-continued

Modifications introduced into the VSV genomic sequence (Genbank accession EF197793) are listed. Note that Line 3 includes a 3 base insertion, which shifts numbering in the recombinant genomic clone (rEF197793). If nucleotide substitutions were introduced to change amino acid coding, the base change in the codon is indicated in red.

```
2701    tgctcaatgt accagagcac ttcagaagac cattcaatat aggtctttac aagggaacga
2761    ttgagctcac aatgaccatc tacgatgatg agtcactgga agcagctcct atgatctggg
2821    atcatttcaa ttcttccaaa ttttctgatt tcagagagaa ggccttaatg tttggcctga
2881    ttgtcgagaa aaaggcatct ggagcttggg tcctggattc tgtcagccac ttcaaatgag
2941    ctagtctagc ttccagcttc tgaacaatcc ccggtttact cagtctctcc taattccagc
3001    ctttcgaaca actaatatcc tgtcttctct atcccgatga aaaaaactaa cagagatcga
3061    tctgtttcct tgacaccatg aagtgccttt tgtacttagc tttttttattc atcggggtga
3121    attgcaagtt caccatagtt tttccacaca accaaaaagg aaactggaaa aatgttcctt
3181    ccaattacca ttattgcccg tcaagctcag atttaaattg gcataatgac ttagtaggca
3241    cagccttaca agtcaaaatg cccaagagtc acaaggctat tcaagcagac ggttggatgt
3301    gtcatgcttc caaatgggtc actacttgtg atttccgctg gtacggaccg aagtatataa
3361    cacattccat ccgatccttc actccatctg tagaacaatg caaggaaagc attgaacaaa
3421    cgaaacaagg aacttggctg aatccaggct tccctcctca aagttgtgga tatgcaactg
3481    tgacggatgc tgaagcagcg attgtccagg tgactcctca ccatgtgctt gttgatgaat
3541    acacaggaga atggggttgat tcacagttca tcaacggaaa atgcagcaat gacatatgcc
3601    ccactgtcca taactccaca acctggcatt ccgactataa ggtcaaaggg ctatgtgatt
3661    ctaacctcat ttccatggac atcaccttct tctcagagga cggagagcta tcatccctag
3721    gaaagaaggg cacagggttc agaagtaact actttgctta tgaaactgga gacaaggcct
3781    gcaaaatgca gtactgcaag cattggggag tcagactccc atcaggtgtc tggttcgaga
3841    tggctgataa ggmtctcttt gctgcagcca gattccctga atgcccagaa gggtcaagta
3901    tctctgctcc atctcagacc tcagtggatg taagtctcat tcaggacgtt gagaggatct
3961    tggattattc cctctgccaa gaaacctgga gcaaaatcag agcgggtctt cccatctctc
4021    cagtggatct cagctatctt gctcctaaaa acccaggaac cggtcctgtc tttaccataa
4081    tcaatggtac cctaaaatac tttgagacca gatacatcag agtcgatatt gctgctccaa
4141    tcctctcaag aatggtcgga atgatcagtg gaactaccac agaaagggta ctgtgggatg
4201    actgggctcc atatgaagac gtggaaattg gacccaatgg agttctgagg accagttcag
4261    gatataagtt tccttatatt atgattggac atggtatgtt ggactccgat cttcatctta
4321    gctcaaaggc tcaggtgttt gaacatcctc acattcaaga cgctgcttcg cagctcctg
4381    atggtgagac tttatttttt ggtgatactg ggctatccaa aaatccaatc gagtttgtag
4441    aaggttggtt cagtagttgg aagagctcta ttgcctcttt tttctttacc atagggttaa
4501    tcattggact attcttggtt ctccgagttg gtatttatct ttgcattaaa ttaaagcaca
4561    ccaagaaaag acagatttat acagacatag agtgaaccg acttggaaag taactcaaat
4621    cctgcacaac agattcttca tgtttgaacc aaatcaactt gtgatatcat gctcaaagag
4681    gccttaatta tattttaatt tttaattttt atgaaaaaaa ctaacagcaa tcatggaagt
4741    ccacgatttt gagaccgacg agttcaatga tttcaatgaa gatgactatg ccacaagaga
4801    attcctgaat cccgatgagc gcatgacgta cttgaatcat cgtgattaca atttgaattc
4861    tcctctaatt agtgatgata ttgacaattt gatcaggaaa ttcaattctc ttccgattcc
4921    ctcgatgtgg gatagtaaga actgggatgg agttcttgag atgttaacat catgtcaagc
4981    caatcccatc tcaacatctc agatgcataa atggatggga agttggttaa tgtctgataa
5041    tcatgatgcc agtcaagggt atagttttttt acatgaagtg gacaaagagg cagaaataac
5101    atttgacgtg gtggagacct tcatccgcgg ctgggggcaac aaaccaattg aatacatcaa
5161    aaaggaaaga tggactgact cattcaaaat tctcgcttat ttgtgtcaaa agtttttgga
5221    cttacacaag ttgacattaa tcttaaatgc tgtctctgag gtggaattgc tcaacttggc
5281    gaggactttc aaaggcaaag tcagaagaag ttctcatgga acgaacatat gcaggattag
5341    ggttccagc ttgggtccta cttttatttc agaaggatgg gcttacttca agaaacttga
5401    tattctaatg gaccgaaact ttctgttaat ggtcaaagat gtgattatag ggaggatgca
5461    aacggtgcta tccatggtat gtagaataga caacctgttc tcagagcaag acatcttctc
5521    ccttctaaat atctacagaa ttggagataa aattgtggag aggcagggaa attttttctta
5581    tgacttgatt aaaatggtgg aaccgatatg caacttgaag ctgatgaaat tagcaagaga
5641    atcaaggcct ttagtcccac aattccctca ttttgaaaat catatcaaga cttctgttga
5701    tgaaggggca aaaattgacc gaggtataag attcctccat gatcagataa tgactgtgaa
5761    aacagtggat ctcacactgg tgatttatgg atcgttcaga cattgggtc atcctttat
5821    agattattac actggactag aaaaattaca ttcccaagta accatgaaga aagatattga
5881    tgtgtcatat gcaaaagcac ttgcaagtga tttagctcgg attgttctat ttcaacagtt
5941    caatgatcat aaaaagtggt tcgtgaatgg agacttgctc cctcatgatc atcccttaa
6001    aagtcatgtt aaagaaaata catggcctac agctgctcaa gttcaagatt ttggagataa
6061    atggcatgaa cttccgctga ttaaatgttt tgaaataccc gacttactag acccatcgat
6121    aatatactct gacaaaagtc attcaatgaa taggtcagag gtgttgaaac atgtccgaat
6181    gaatccgaac actcctatcc ctagtaaaaa ggtgttgcag actatgttgg acacaaaggc
6241    taccaattgg aaagaatttc ttaaagagat tgatgagaag ggcttagatg atgatgatct
6301    aattattggt cttaaaggaa aggagaggga actgaagttg gcaggtagat ttttctccct
6361    aatgtcttgg aaattgcgag aatactttgt aattaccgaa tatttgataa agactcattt
6421    cgtccctatg tttaaaggcc tgacaatggc ggacgatcta actgcagtca ttaaaaagat
6481    gttagattcc tcatccgcc aaggattgaa gtcatatgag gcaatttgca tagccaatca
6541    cattgattac gaaaaatgga ataaccacca aaggaagtta tcaaacggcc agtgttccg
6601    agttatgggc cagttcttag gttatccatc cttaatcgag agaactcatg aatttttttga
6661    gaaagtcttt atatactaca atgaagacc agatgctgtc gtgttcaca acaacacact
6721    gatcaattca acctcccaac gagtttgttg gcaaggacaa gaggttggac tggaaggtct
6781    acggcaaaaa ggatggagta tcctcaatct actggttatt caagagagg ctaaaatcag
6841    aaacactgct gtcaaagtct ggcacaagg tgataatcaa gttatttgca cacagtataa
6901    aacgaagaaa tcgagaaacg ttgtagaatt acagggtgct ctcaatcaaa tggtttctaa
6961    taatgagaaa attatgactg caatcaaaat agggacaggg aagttaggac ttttgataaa
```

TABLE 1-continued

Modifications introduced into the VSV genomic sequence (Genbank accession EF197793) are listed. Note that

Example 2: VSV Genome and Cloning Fragments

Figure 2A:
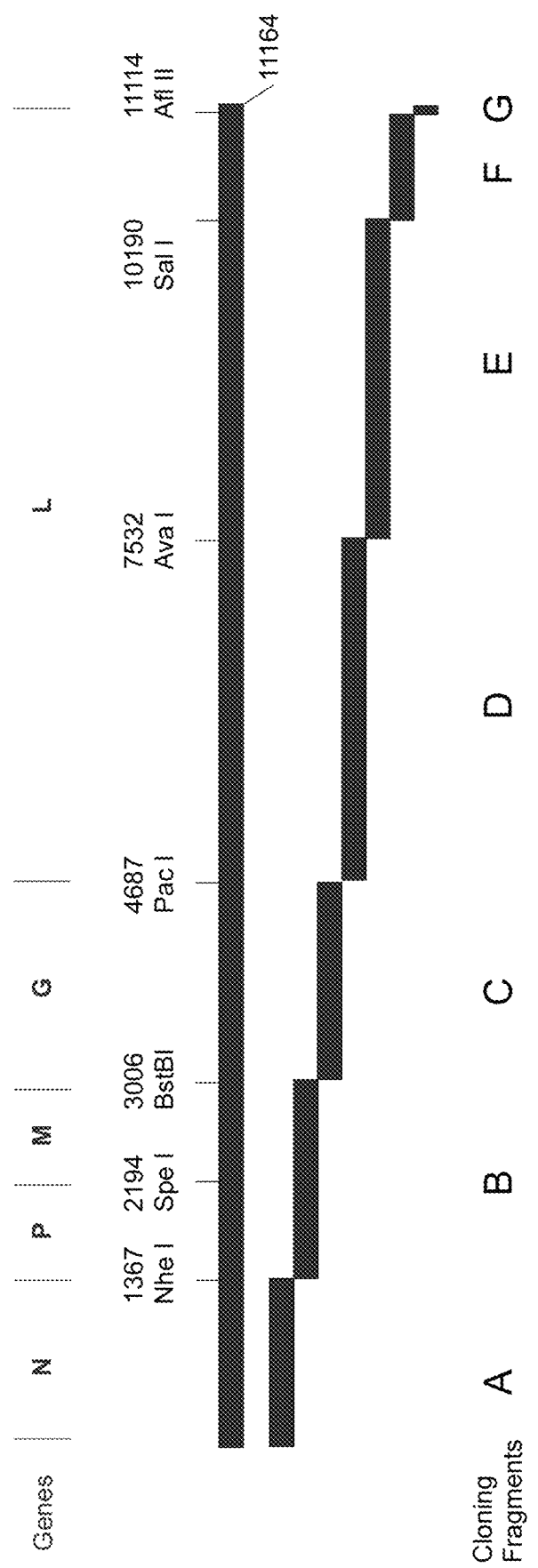
FIG. 2A depicts a schematic VSV genome and cloning fragments where fragments A and G are combined to produce fragment VSV-AG. The AG fragment may be cloned first. There are BsmBI sites added to the termini of AG fragment, which may be used to add ribozyme sequences to the termini without addition of nucleotides introduced by the restriction enzyme cleavage site. There may be a polylinker added between the combined A-G fragments (NheI-BstBI-PacI-AvaI-SalI-AflII). After cloning the VSV-AG fragment into the Dual Ribozyme vector, B through F may be inserted in subsequent cloning steps.

FIG. 2A depicts a schematic of a VSV genome and cloning fragments.

In the sequences provided in FIGS. 2B-2G, terminal fragments A and G are combined to produce fragment VSV-AG.

The DNA fragments are designed for cloning into pSP72 or other similar cloning vectors. Before adding VSV cDNA sequences, the cloning plasmid is modified by insertion of the hammerhead and hepatitis delta virus ribozyme sequences. A BsmBI restriction enzyme cleavage site is placed between the ribozyme sequences (5'-hammerhead ribozyme-BsmBI-hepatitis delta virus ribozyme-3') for the purpose of inserting the VSV-AG fragment.

The AG fragment was designed with BsmBI sites at the 5' and 3' termini (lower case nucleotides) for insertion between the ribozyme sequences introduced in the step above. Because BsmBI cleaves distal to its recognition sequence (see bullet below), this enzyme may be used to join the AG fragment directly to the ribozymes while also eliminating the non-VSV nucleotides added to create the enzyme cleavage signal. (Ball L A, Pringle C R, Flanagan B, Perepelitsa V P, Wertz G W. Phenotypic consequences of rearranging the P, M, and G genes of vesicular stomatitis virus. J Virol. 1999 June; 73 (6): 4705-12, the disclosure of which is incorporated by reference).

Like other restriction endonucleases of this type (BspMI, EarI, PleI, SfaNI and others), BsmBI cleaves distal to its recognition sequence:

```
5'-CGTCTC/N-3'
                                          (SEQ ID NO: 18)
3'-GCAGAGNNNNN/N-5'
```

N is any nucleotide and/indicates cleavage site.

The VSV-AG fragment also is designed to facilitate subsequent cloning. Between the fused A and G fragments there is a polylinker sequence (noted in red nucleotides) that contains restriction endonuclease cleavage sites needed for sequential cloning of Fragments B-F to assemble a full-length clone. The polylinker contains 5'-NheI-BstBI-PacI-AvaI-SalI-AflIII-3' restriction endonuclease cleavage sites. Polylinker nucleotides are replaced by VSV genomic sequence as the full-length clone is assembled.

Example 3: Virus Rescue Support Plasmid Insert Optimization

Strategy for optimizing gene inserts encoding VSV N, P, M, G, and L for construction of plasmid DNAs encoding trans-acting proteins needed to initiate virus rescue. Gene inserts were optimized using steps in Example 4 then synthesized by a contract lab and subsequently cloned into a plasmid under the control of the hCMV promoter and enhancer.

Example 4: Coding Sequence Optimization and Gene Design

Step 1. Replace VSV sequence with codons used by highly expressed mammalian genes. Use the CodonJuggle program found in the GeneDesign Webtool (Richardson et al. 2010. Nucleic Acids Res 38:2603-2606 and Richardson et al. 2006. Genome Res 16:550-556).

Step 2. Eliminate potential RNA processing signals in the coding sequence that might direct unwanted RNA splicing or cleavage/polyadenylation reaction.
  a) Identify potential splice site signals and remove by introducing synonymous codons. Splice site predictions were made with the webtool at the Berkeley Drosophila Genome Project website (Reese et al. 1997. J Comput Biol 4:311-323).
  b) Scan the insert for consensus cleavage/polyadenylation signals (AAUAAA) (Zhao et al. 1999. MMBR 63:405-445). Disrupt by introducing synonymous codons.

Step 3
  a) Add a preferred translational start sequence (the Kozak sequence) (Kochetov et al. 1998. FEBS letters 440: 351-355, Kozak. 1999. Gene 234:187-208, Kozak. 1991. J Biol Chem 266:19867-19870 and Zhang. 1998. Human molecular genetics 7:919-932).
  b) Add a preferred translational stop codon at the 3' end (Kochetov et al. 1998. FEBS letters 440:351-355, Sun et al. 2005. J Mol Evol 61:437-444 and Zhang. 1998. Human molecular genetics 7:919-932).

Step 4. Scan the sequence for homopolymeric stretches of 5 nucleotides or more. Interrupt these sequences by introducing synonymous codons.

Step 5. Scan the sequence for restriction endonuclease cleavage sites and eliminate any unwanted recognitions signals.

Step 6. Confirm that the modified sequence translates into the expected amino acid sequence.

The invention is further described by the following numbered paragraphs:

1. A vesicular stomatitis virus (VSV) genomic clone comprising:
   (a) a VSV genome encoding and expressing a nucleocapsid, phosphoprotein, matrix, glycoprotein and large protein, wherein the VSV genome comprises nucleotide substitutions and amino acid coding changes to improve replicative fitness and genetic stability,
   (b) a cloning vector,
   (c) an extended T7 promoter,
   (d) a hammerhead ribozyme,
   (e) a hepatitis delta virus ribozyme and T7 terminator
   (f) unique restriction endonuclease cleavage sites in a VSV genomic sequence
   (g) a leader and a trailer that are cis-acting sequences controlling mRNA synthesis and replication 2. The VSV genomic clone of paragraph 1, wherein the cloning vector is pSP72 (Genbank X65332.2)

3. The VSV genomic clone of paragraph 1 or 2, wherein the extended T7 promoter is PT7-g10.

4. The VSV genomic clone of any one of paragraphs 1 to 3, wherein the unique restriction endonuclease cleavage sites are 1367 NheI, 2194 SpeI, 2194 BstBI, 4687 PacI, 7532 AvaI, 10190 SalI and 11164 AflIII.

5. The VSV genomic clone of any one of paragraphs 1 to 4, wherein the VSV genomic clone is depicted in FIG. 1.

6. The VSV genomic clone of any one of paragraphs 1 to 5, wherein the nucleotide position is according to GenBank Accession Number EF197793 and wherein the nucleotide substitutions are selected from the group consisting of
   1371 CA>GC (NheI)
   After 2195 insert TAG (SpeI) (all genome numbers below adjusted to include +3 bp)
   3036 G>T improves match to consensus transcription stop signal 3853 X>A (was an ambiguity in Genbank file)
4691 T>A to generate PacI
7546 C>A silent change in L coding sequence eliminates a BstBI site
1960 TAC>TCC to change Y>S
3247 GTA>ATA to change V>I
3729 AAG>GAG to change K>E
4191 GTA>GAA to change V>E
4386 GGT>GAT to change G>D
4491 ACC>ATC to change T>I
5339 ATT>CTT to change I>L
5834 ACT>GCT to change T>A and
10959 AGA>AAA to change R>K.

7. The VSV genomic clone of any one of paragraphs 1 to 6, wherein the nucleotide position is according to GenBank Accession Number EF197793 and wherein the nucleotide substitutions are selected from the group consisting of:

| | Nucleotide position in EF197793 | Nucleotide position in rEF197793 | Nucleotide Change | Purpose |
|---|---|---|---|---|
| 1 | Substitution 1371-2 | Substitution 1371-2 | CA > GC | Creates a unique NheI cleavage site between N and P gens |
| 2 | Substitution 1960-2 | Substitution 1960-2 | TAC > TCC | Y > S substitution in P protein amino acid sequence to agree with consensus. |
| 3 | Insert after 2195 | 3 base insert after 2195 | Insert TAG | Creates a unique SpeI site between P and M genes |
| 4 | Substitution 3039 | Substitution 3042 | G > T | Improves agreement with consensus. Also improves agreement with consensus transcription stop signal |
| 5 | Substitution 3234-6 | Substitution 3237-9 | GTA > ATA | V > I substitution in P protein amino acid sequence to agree with consensus. |
| 6 | Substitution 3729-31 | Substitution 3732-34 | AAG > GAG | K > E substitution in G protein amino acid sequence to agree with consensus. |
| 7 | Substitution 3856 | Substitution 3859 | N > A | Replace unknown base in Genbank file with consensus |
| 8 | Substitution 4191-93 | Substitution 4194-6 | GTA > GAA | V > E substitution in G protein amino acid sequence to agree with consensus. |
| 9 | Substitution 4386-88 | Substitution 4389-92 | GGT > GAT | G > D substitution in G protein amino acid sequence to agree with consensus. |
| 10 | Substitution 4491-93 | Substitution 4494-96 | ACC > ATC | T > I substitution in G protein amino acid sequence to agree with consensus. |
| 11 | Substitution 4694 | Substitution 4697 | T > A | Creates unique PacI cleavage site between G and L genes |
| 12 | Substitution 5339-41 | Substitution 5342-44 | ATT > CTT | I > L substitution in L protein amino acid sequence to agree with consensus. |
| 13 | Substitution 5834-6 | Substitution 5837-40 | ACT > GCT | T > A substitution in L protein amino acid sequence to agree with consensus. |
| 14 | Substitution 10959-61 | Substitution 10962-64 | AGA > AAA | R > K substitution in L protein amino acid sequence to agree with consensus. |
| 15 | Substitution 7546 | Substitution 7549 | C > A | Eliminates a BstBI site in the L gene sequence making the BstBI site between the M and G genes unique. This substitution was silent for amino acid coding. |

8. The VSV genomic clone of any one of paragraphs 1 to 7, wherein the nucleotide sequences of the VSV genome encoding and expressing a nucleocapsid, phosphoprotein, matrix, glycoprotein and large protein are selected from the group consisting of FIGS. 2B-2G.

9. The VSV genomic clone of any one of paragraphs 1 to 7, wherein the nucleotide sequences of the VSV genome encoding and expressing a nucleocapsid, phosphoprotein, matrix, glycoprotein and large protein are selected from the group consisting of FIGS. 3A-3G, 10. A method for rescuing VSV comprising combining a T7 RNA polymerase promoter and a hammerhead ribozyme sequence to increase the efficiency of synthesis and processing of full-length VSV genomic RNA in transfected cells.

11. The method of paragraph 10, wherein the T7 RNA polymerase promoter is a minimal functional sequence designed to initiate transcription very close to or precisely at the 5' terminus of the genomic clone.

12. The method of paragraph 11, wherein the T7 promoter is a T7 promoter sequence that enhances formation of stable initiation and elongation complexes and a hammerhead ribozyme sequence at the 5' terminus that catalyzes removal of extra nucleotides restoring the authentic 5' terminus of the genomic transcript.

13. The method of any one of paragraphs 10 to 12, wherein the plasmids encoding VSV nucleocapsid, phosphoprotein, matrix, glycoprotein and large protein are optimized to improve expression of the trans-acting proteins to initiate virus rescue.

14. The method of paragraph 13, where the optimization is codon optimization.

15. The method of paragraph 14, wherein the codon optimization comprises replacing a VSV nucleotide sequence with codons used by highly expressed mammalian genes.

16. The method of paragraph 14 or 15, wherein the codon optimization comprises eliminating potential RNA processing signals in the coding sequence that might direct unwanted RNA splicing or cleavage/polyadenylation reaction, wherein the eliminating comprises:

(a) identifying potential splice site signals and remove by introducing synonymous codons and/or (b) scanning an insert for consensus cleavage/polyadenylation signals (AAUAAA) and introducing synonymous codons to disrupt the consensus cleavage/polyadenylation signals.

17. The method of any one of paragraphs 14 to 16, wherein the codon optimization comprises (a) adding a preferred translational start sequence (the Kozak sequence) and/or (b) adding a preferred translational stop codon.

18. The method of any one of paragraphs 14 to 17, wherein the codon optimization comprises scanning a sequence for homopolymeric stretches of 5 nucleotides or more and interrupting the sequences by introducing synonymous codons.

19. The method of any one of paragraphs 14 to 18, wherein the codon optimization comprises scanning a sequence for restriction endonuclease cleavage sites and eliminate any unwanted recognitions signals.

20. The method of any one of paragraphs 14 to 19, wherein the codon optimization comprises confirming that a modified sequence translates into an expected amino acid sequence.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
<160> NUMBER OF SEQ ID NOS: 18

<210> SEQ ID NO 1
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240
```

Arg Gly Ile Ile Ala Ala Leu Gly Pro Asp Gly Lys Pro Ser Arg Ile
            245                 250                 255

Val Val Ile Tyr Thr Thr Gly Ser Gln Ala Thr Met Asp Glu Arg Asn
        260                 265                 270

Arg Gln Ile Ala Glu Ile Gly Ala Ser Leu Ile Lys His Trp
        275                 280                 285

<210> SEQ ID NO 2
<211> LENGTH: 2462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaactcgagc agctgaagct tgcatgcctg caggtcgact ctagaggatc cccgggtacc      60
gagctcgaat tcatcgatga tatcagatct gccggtctcc ctatagtgag tcgtattaat    120
ttcgataagc caggttaacc tgcattaatg aatcggccaa cgcgcgggga gaggcggttt    180
gcgtattggg cgctcttccg cttcctcgct cactgactcg ctgcgctcgg tcgttcggct    240
gcggcgagcg gtatcagctc actcaaaggc ggtaatacgg ttatccacag aatcagggga    300
taacgcagga agaacatgt gagcaaaagg ccagcaaaag gccaggaacc gtaaaaaggc    360
cgcgttgctg gcgttttttcc ataggctccg ccccccctgac gagcatcaca aaaatcgacg    420
ctcaagtcag aggtggcgaa acccgacagg actataaaga taccaggcgt ttccccctgg    480
aagctccctc gtgcgctctc ctgttccgac cctgccgctt accggatacc tgtccgcctt    540
tctcccttcg ggaagcgtgg cgctttctca gctcacgc tgtaggtatc tcagttcggt    600
gtaggtcgtt cgctccaagc tgggctgtgt gcacgaaccc cccgttcagc ccgaccgctg    660
cgccttatcc ggtaactatc gtcttgagtc aacccggta agacacgact tatcgccact    720
ggcagcagcc actggtaaca ggattagcag agcgaggtat gtaggcggtg ctacagagtt    780
cttgaagtgg tggcctaact acggctacac tagaagaaca gtatttggta tctgcgctct    840
gctgaagcca gttaccttcg gaaaaagagt tggtagctct tgatccggca acaaaccac    900 cgctggtagc ggtggttttt ttgtttgcaa gcagcagatt acgcgcagaa aaaaaggatc    960
tcaagaagat cctttgatct tttctacggg gtctgacgct cagtggaacg aaaactcacg   1020
ttaagggatt ttggtcatga gattatcaaa aaggatcttc acctagatcc ttttaaatta   1080
aaaatgaagt tttaaatcaa tctaaagtat atatgagtaa acttggtctg acagttacca   1140
atgcttaatc agtgaggcac ctatctcagc gatctgtcta tttcgttcat ccatagttgc   1200
ctgactcccc gtcgtgtaga taactacgat acgggagggc ttaccatctg gccccagtgc   1260
tgcaatgata ccgcgagacc cacgctcacc ggctccagat ttatcagcaa taaaccagcc   1320
agccggaagg gccgagcgca gaagtggtcc tgcaacttta tccgcctcca tccagtctat   1380
taattgttgc cgggaagcta gagtaagtag ttcgccagtt aatagtttgc gcaacgttgt   1440
tgccattgct acaggcatcg tggtgtcacg ctcgtcgttt ggtatggctt cattcagctc   1500
cggttcccaa cgatcaaggc gagttacatg atccccatg ttgtgcaaaa aagcggttag   1560
ctccttcggt cctccgatcg ttgtcagaag taagttggcc gcagtgttat cactcatggt   1620
tatggcagca ctgcataatt ctcttactgt catgccatcc gtaagatgct tttctgtgac   1680
tggtgagtac tcaaccaagt cattctgaga atagtgtatg cggcgaccga gttgctcttg   1740
cccggcgtca atacgggata ataccgcgcc acatagcaga actttaaaag tgctcatcat   1800

-continued

```
tggaaaacgt tcttcggggc gaaaactctc aaggatctta ccgctgttga gatccagttc    1860
gatgtaaccc actcgtgcac ccaactgatc ttcagcatct tttactttca ccagcgtttc    1920
tgggtgagca aaacaggaa ggcaaaatgc cgcaaaaaag gaataaggg cgacacggaa      1980
atgttgaata ctcatactct tccttttca atattattga agcatttatc agggttattg    2040
tctcatgagc ggatacatat ttgaatgtat ttagaaaaat aaacaaatag gggttccgcg   2100
cacatttccc cgaaaagtgc cacctgacgt ctaagaaacc attattatca tgacattaac    2160
ctataaaaat aggcgtatca cgaggccctt tcgtctcgcg cgtttcggtg atgacggtga    2220
aaacctctga cacatgcagc tcccggagac ggtcacagct tgtctgtaag cggatgccgg    2280
gagcagacaa gcccgtcagg gcgcgtcagc gggtgttggc gggtgtcggg gctggcttaa    2340
ctatgcggca tcagagcaga ttgtactgag agtgcaccat atggacatat tgtcgttaga    2400
acgcggctac aattaataca taaccttatg tatcatacac atacgattta ggtgacacta    2460
ta                                                                   2462
```

<210> SEQ ID NO 3
<211> LENGTH: 422
<212> TYPE: PRT
<213> ORGANISM: Vesicular stomatitis Indiana virus

<400> SEQUENCE: 3

```
Met Ser Val Thr Val Lys Arg Ile Ile Asp Asn Thr Val Ile Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
        35                  40                  45

Ser Asp Leu Arg Gly Tyr Val Tyr Gln Gly Leu Lys Ser Gly Asn Val
    50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Arg Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205

Glu Cys Ala Ser Phe Arg Tyr Gly Thr Ile Val Ser Arg Phe Lys Asp
    210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
```

```
              245                 250                 255
Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
        275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Ser Lys Tyr Thr Pro Asp Asp Ser Thr Gly Gly Leu Thr Thr Asn Ala
        355                 360                 365

Pro Pro Gln Gly Arg Asp Val Val Glu Trp Leu Gly Trp Phe Glu Asp
    370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420

<210> SEQ ID NO 4
<211> LENGTH: 265
<212> TYPE: PRT
<213> ORGANISM: Vesicular stomatitis Indiana virus

<400> SEQUENCE: 4

Met Asp Asn Leu Thr Lys Val Arg Glu Tyr Leu Lys Ser Tyr Ser Arg
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Arg Pro Ser Tyr Phe Gln Ala Ala Asp Asp Ser Asp Thr Glu Ser
    50                  55                  60

Glu Pro Glu Ile Glu Asp Asn Gln Gly Leu Tyr Val Pro Asp Pro Glu
65                  70                  75                  80

Ala Glu Gln Val Glu Gly Phe Ile Gln Gly Pro Leu Asp Asp Tyr Ala
                85                  90                  95

Asp Glu Asp Val Asp Val Val Phe Thr Ser Asp Trp Lys Gln Pro Glu
            100                 105                 110

Leu Glu Ser Asp Glu His Gly Lys Thr Leu Arg Leu Thr Leu Pro Glu
        115                 120                 125

Gly Leu Ser Gly Glu Gln Lys Ser Gln Trp Leu Leu Thr Ile Lys Ala
    130                 135                 140

Val Val Gln Ser Ala Lys His Trp Asn Leu Ala Glu Cys Thr Phe Glu
145                 150                 155                 160

Ala Ser Gly Glu Gly Val Ile Ile Lys Lys Arg Gln Ile Thr Pro Asp
                165                 170                 175

Val Tyr Lys Val Thr Pro Val Met Asn Thr His Pro Tyr Gln Ser Glu
            180                 185                 190
```

```
Ala Val Ser Asp Val Trp Ser Leu Ser Lys Thr Ser Met Thr Phe Gln
            195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Gly Asn Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

<210> SEQ ID NO 5
<211> LENGTH: 229
<212> TYPE: PRT
<213> ORGANISM: Vesicular stomatitis Indiana virus

<400> SEQUENCE: 5

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Asn
            20                  25                  30

Met Glu Tyr Ala Pro Ser Ala Pro Ile Asp Lys Ser Tyr Phe Gly Val
        35                  40                  45

Asp Glu Met Asp Thr His Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Ala His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
    210                 215                 220

Val Ser His Phe Lys
225

<210> SEQ ID NO 6
<211> LENGTH: 511
<212> TYPE: PRT
<213> ORGANISM: Vesicular stomatitis Indiana virus
<220> FEATURE:
<221> NAME/KEY: MOD_RES
<222> LOCATION: (259)..(259)
<223> OTHER INFORMATION: Any amino acid

<400> SEQUENCE: 6
```

-continued

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

Val Pro Ser Asn Tyr His Tyr Cys Pro Ser Ser Asp Leu Asn Trp
            35                  40              45

His Asn Asp Leu Val Gly Thr Ala Leu Gln Val Lys Met Pro Lys Ser
    50                  55                  60

His Lys Ala Ile Gln Ala Asp Gly Trp Met Cys His Ala Ser Lys Trp
65              70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Lys Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Xaa Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Val Leu Trp Asp Asp Trp Ala Pro Tyr Glu Asp Val Glu Ile
370                 375                 380

Gly Pro Asn Gly Val Leu Arg Thr Ser Gly Tyr Lys Phe Pro Leu
385                 390                 395                 400

Tyr Met Ile Gly His Gly Met Leu Asp Ser Asp Leu His Leu Ser Ser
                405                 410                 415
```

```
Lys Ala Gln Val Phe Glu His Pro His Ile Gln Asp Ala Ala Ser Gln
                420                 425                 430
Leu Pro Asp Gly Glu Thr Leu Phe Phe Gly Asp Thr Gly Leu Ser Lys
            435                 440                 445
Asn Pro Ile Glu Phe Val Glu Gly Trp Phe Ser Ser Trp Lys Ser Ser
        450                 455                 460
Ile Ala Ser Phe Phe Phe Thr Ile Gly Leu Ile Ile Gly Leu Phe Leu
465                 470                 475                 480
Val Leu Arg Val Gly Ile Tyr Leu Cys Ile Lys Leu Lys His Thr Lys
                485                 490                 495
Lys Arg Gln Ile Tyr Thr Asp Ile Glu Met Asn Arg Leu Gly Lys
                500                 505                 510

<210> SEQ ID NO 7
<211> LENGTH: 2109
<212> TYPE: PRT
<213> ORGANISM: Vesicular stomatitis Indiana virus

<400> SEQUENCE: 7

Met Glu Val His Asp Phe Glu Thr Asp Glu Phe Asn Asp Phe Asn Glu
1               5                   10                  15
Asp Asp Tyr Ala Thr Arg Glu Phe Leu Asn Pro Asp Glu Arg Met Thr
            20                  25                  30
Tyr Leu Asn His Ala Asp Tyr Asn Leu Asn Ser Pro Leu Ile Ser Asp
        35                  40                  45
Asp Ile Asp Asn Leu Ile Arg Lys Phe Asn Ser Leu Pro Ile Pro Ser
    50                  55                  60
Met Trp Asp Ser Lys Asn Trp Asp Gly Val Leu Glu Met Leu Thr Ser
65                  70                  75                  80
Cys Gln Ala Asn Pro Ile Ser Thr Ser Gln Met His Lys Trp Met Gly
                85                  90                  95
Ser Trp Leu Met Ser Asp Asn His Asp Ala Ser Gln Gly Tyr Ser Phe
            100                 105                 110
Leu His Glu Val Asp Lys Glu Ala Glu Ile Thr Phe Asp Val Val Glu
        115                 120                 125
Thr Phe Ile Arg Gly Trp Gly Asn Lys Pro Ile Glu Tyr Ile Lys Lys
    130                 135                 140
Glu Arg Trp Thr Asp Ser Phe Lys Ile Leu Ala Tyr Leu Cys Gln Lys
145                 150                 155                 160
Phe Leu Asp Leu His Lys Leu Thr Leu Ile Leu Asn Ala Val Ser Glu
                165                 170                 175
Val Glu Leu Leu Asn Leu Ala Arg Thr Phe Lys Gly Lys Val Arg Arg
            180                 185                 190
Ser Ser His Gly Thr Asn Ile Cys Arg Ile Arg Val Pro Ser Leu Gly
        195                 200                 205
Pro Thr Phe Ile Ser Glu Gly Trp Ala Tyr Phe Lys Lys Leu Asp Ile
    210                 215                 220
Leu Met Asp Arg Asn Phe Leu Leu Met Val Lys Asp Val Ile Ile Gly
225                 230                 235                 240
Arg Met Gln Thr Val Leu Ser Met Val Cys Arg Ile Asp Asn Leu Phe
                245                 250                 255
Ser Glu Gln Asp Ile Phe Ser Leu Leu Asn Ile Tyr Arg Ile Gly Asp
            260                 265                 270
Lys Ile Val Glu Arg Gln Gly Asn Phe Ser Tyr Asp Leu Ile Lys Met
        275                 280                 285
```

-continued

Val Glu Pro Ile Cys Asn Leu Lys Leu Met Lys Leu Ala Arg Glu Ser
    290             295             300

Arg Pro Leu Val Pro Gln Phe Pro His Phe Glu Asn His Ile Lys Thr
305             310             315             320

Ser Val Asp Glu Gly Ala Lys Ile Asp Arg Gly Ile Arg Phe Leu His
            325             330             335

Asp Gln Ile Met Ser Val Lys Thr Val Asp Leu Thr Leu Val Ile Tyr
            340             345             350

Gly Ser Phe Arg His Trp Gly His Pro Phe Ile Asp Tyr Tyr Thr Gly
        355             360             365

Leu Glu Lys Leu His Ser Gln Val Thr Met Lys Lys Asp Ile Asp Val
    370             375             380

Ser Tyr Ala Lys Ala Leu Ala Ser Asp Leu Ala Arg Ile Val Leu Phe
385             390             395             400

Gln Gln Phe Asn Asp His Lys Lys Trp Phe Val Asn Gly Asp Leu Leu
            405             410             415

Pro His Asp His Pro Phe Lys Ser His Val Lys Glu Asn Thr Trp Pro
            420             425             430

Thr Ala Ala Gln Val Gln Asp Phe Gly Asp Lys Trp His Glu Leu Pro
        435             440             445

Leu Ile Lys Cys Phe Glu Ile Pro Asp Leu Leu Asp Pro Ser Ile Ile
    450             455             460

Tyr Ser Asp Lys Ser His Ser Met Asn Arg Ser Glu Val Leu Lys His
465             470             475             480

Val Arg Met Asn Pro Asn Thr Pro Ile Pro Ser Lys Lys Val Leu Gln
            485             490             495

Thr Met Leu Asp Thr Lys Ala Thr Asn Trp Lys Glu Phe Leu Lys Glu
            500             505             510

Ile Asp Glu Lys Gly Leu Asp Asp Asp Leu Ile Ile Gly Leu Lys
        515             520             525

Gly Lys Glu Arg Glu Leu Lys Leu Ala Gly Arg Phe Phe Ser Leu Met
    530             535             540

Ser Trp Lys Leu Arg Glu Tyr Phe Val Ile Thr Glu Tyr Leu Ile Lys
545             550             555             560

Thr His Phe Val Pro Met Phe Lys Gly Leu Thr Met Ala Asp Asp Leu
            565             570             575

Thr Ala Val Ile Lys Lys Met Leu Asp Ser Ser Ser Gly Gln Gly Leu
            580             585             590

Lys Ser Tyr Glu Ala Ile Cys Ile Ala Asn His Ile Asp Tyr Glu Lys
        595             600             605

Trp Asn Asn His Gln Arg Lys Leu Ser Asn Gly Pro Val Phe Arg Val
    610             615             620

Met Gly Gln Phe Leu Gly Tyr Pro Ser Leu Ile Glu Arg Thr His Glu
625             630             635             640

Phe Phe Glu Lys Ser Leu Ile Tyr Tyr Asn Gly Arg Pro Asp Leu Met
            645             650             655

Arg Val His Asn Asn Thr Leu Ile Asn Ser Thr Ser Gln Arg Val Cys
            660             665             670

Trp Gln Gly Gln Glu Gly Gly Leu Glu Gly Leu Arg Gln Lys Gly Trp
        675             680             685

Ser Ile Leu Asn Leu Leu Val Ile Gln Arg Glu Ala Lys Ile Arg Asn
    690             695             700

-continued

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
                740                 745                 750

Ile Gly Thr Gly Lys Leu Gly Leu Leu Ile Asn Asp Asp Glu Thr Met
                755                 760                 765

Gln Ser Ala Asp Tyr Leu Asn Tyr Gly Lys Ile Pro Ile Phe Arg Gly
770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
                820                 825                 830

Met Ile Gln Tyr Asn Tyr Phe Gly Thr Phe Ala Arg Leu Leu Leu Met
                835                 840                 845

Met His Asp Pro Ala Leu Arg Gln Ser Leu Tyr Glu Val Gln Asp Lys
850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
                900                 905                 910

Phe Ile His Val His Ala Arg Ser Glu His Leu Lys Glu Met Ser Ala
                915                 920                 925

Val Phe Gly Asn Pro Glu Ile Ala Lys Phe Arg Ile Thr His Ile Asp
                930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
                980                 985                 990

Tyr His Glu Glu Asp Arg Leu Arg Ser Phe Leu Trp Ser Ile Asn Pro
                995                 1000                1005

Leu Phe Pro Arg Phe Leu Ser Glu Phe Lys Ser Gly Thr Phe Leu
     1010                1015               1020

Gly Val Ala Asp Gly Leu Ile Ser Leu Phe Gln Asn Ser Arg Thr
     1025                1030               1035

Ile Arg Asn Ser Phe Lys Lys Lys Tyr His Arg Glu Leu Asp Asp
     1040                1045               1050

Leu Ile Val Arg Ser Glu Val Ser Ser Leu Thr His Leu Gly Lys
     1055                1060               1065

Leu His Leu Arg Arg Gly Ser Cys Lys Met Trp Thr Cys Ser Ala
     1070                1075               1080

Thr His Ala Asp Thr Leu Arg Tyr Lys Ser Trp Gly Arg Thr Val
     1085                1090               1095

Ile Gly Thr Thr Val Pro His Pro Leu Glu Met Leu Gly Pro Gln
     1100                1105               1110

His Arg Lys Glu Thr Pro Cys Ala Pro Cys Asn Thr Ser Gly Phe

-continued

```
            1115                1120                1125
Asn Tyr Val Ser Val His Cys Pro Asp Gly Ile His Asp Val Phe
        1130                1135                1140
Ser Ser Arg Gly Pro Leu Pro Ala Tyr Leu Gly Ser Lys Thr Ser
        1145                1150                1155
Glu Ser Thr Ser Ile Leu Gln Pro Trp Glu Arg Glu Ser Lys Val
        1160                1165                1170
Pro Leu Ile Lys Arg Ala Thr Arg Leu Arg Asp Ala Ile Ser Trp
        1175                1180                1185
Phe Val Glu Pro Asp Ser Lys Leu Ala Met Thr Ile Leu Ser Asn
        1190                1195                1200
Ile His Ser Leu Thr Gly Glu Glu Trp Thr Lys Arg Gln His Gly
        1205                1210                1215
Phe Lys Arg Thr Gly Ser Ala Leu His Arg Phe Ser Thr Ser Arg
        1220                1225                1230
Met Ser His Gly Gly Phe Ala Ser Gln Ser Thr Ala Ala Leu Thr
        1235                1240                1245
Arg Leu Met Ala Thr Thr Asp Thr Met Arg Asp Leu Gly Asp Gln
        1250                1255                1260
Asn Phe Asp Phe Leu Phe Gln Ala Thr Leu Leu Tyr Ala Gln Ile
        1265                1270                1275
Thr Thr Thr Val Ala Arg Asp Gly Trp Ile Thr Ser Cys Thr Asp
        1280                1285                1290
His Tyr His Ile Ala Cys Lys Ser Cys Leu Arg Pro Ile Glu Glu
        1295                1300                1305
Ile Thr Leu Asp Ser Ser Met Asp Tyr Thr Pro Pro Asp Val Ser
        1310                1315                1320
His Val Leu Lys Thr Trp Arg Asn Gly Glu Gly Ser Trp Gly Gln
        1325                1330                1335
Glu Ile Lys Gln Ile Tyr Pro Leu Glu Gly Asn Trp Lys Asn Leu
        1340                1345                1350
Ala Pro Ala Glu Gln Ser Tyr Gln Val Gly Arg Cys Ile Gly Phe
        1355                1360                1365
Leu Tyr Gly Asp Leu Ala Tyr Arg Lys Ser Thr His Ala Glu Asp
        1370                1375                1380
Ser Ser Leu Phe Pro Leu Ser Ile Gln Gly Arg Ile Arg Gly Arg
        1385                1390                1395
Gly Phe Leu Lys Gly Leu Leu Asp Gly Leu Met Arg Ala Ser Cys
        1400                1405                1410
Cys Gln Val Ile His Arg Arg Ser Leu Ala His Leu Lys Arg Pro
        1415                1420                1425
Ala Asn Ala Val Tyr Gly Gly Leu Ile Tyr Leu Ile Asp Lys Leu
        1430                1435                1440
Ser Val Ser Pro Pro Phe Leu Ser Leu Thr Arg Ser Gly Pro Ile
        1445                1450                1455
Arg Asp Glu Leu Glu Thr Ile Pro His Lys Ile Pro Thr Ser Tyr
        1460                1465                1470
Pro Thr Ser Asn Arg Asp Met Gly Val Ile Val Arg Asn Tyr Phe
        1475                1480                1485
Lys Tyr Gln Cys Arg Leu Glu Lys Gly Lys Tyr Arg Ser His
        1490                1495                1500
Tyr Ser Gln Leu Trp Leu Phe Ser Asp Val Leu Ser Ile Asp Phe
        1505                1510                1515
```

-continued

Ile Gly Pro Phe Ser Ile Ser Thr Thr Leu Leu Gln Ile Leu Tyr
1520            1525                1530

Lys Pro Phe Leu Ser Gly Lys Asp Lys Asn Glu Leu Arg Glu Leu
1535            1540                1545

Ala Asn Leu Ser Ser Leu Leu Arg Ser Gly Glu Gly Trp Glu Asp
1550            1555                1560

Ile His Val Lys Phe Phe Thr Lys Asp Ile Leu Leu Cys Pro Glu
1565            1570                1575

Glu Ile Arg His Ala Cys Lys Phe Gly Ile Ala Lys Asp Asn Asn
1580            1585                1590

Lys Asp Met Ser Tyr Pro Pro Trp Gly Arg Glu Ser Arg Gly Thr
1595            1600                1605

Ile Thr Thr Ile Pro Val Tyr Tyr Thr Thr Pro Tyr Pro Lys
1610            1615                1620

Met Leu Glu Met Pro Pro Arg Ile Gln Asn Pro Leu Leu Ser Gly
1625            1630                1635

Ile Arg Leu Gly Gln Leu Pro Thr Gly Ala His Tyr Lys Ile Arg
1640            1645                1650

Ser Ile Leu His Gly Met Gly Ile His Tyr Arg Asp Phe Leu Ser
1655            1660                1665

Cys Gly Asp Gly Ser Gly Gly Met Thr Ala Ala Leu Leu Arg Glu
1670            1675                1680

Asn Val His Ser Arg Gly Ile Phe Asn Ser Leu Leu Glu Leu Ser
1685            1690                1695

Gly Ser Val Met Arg Gly Ala Ser Pro Glu Pro Ser Ala Leu
1700            1705                1710

Glu Thr Leu Gly Gly Asp Lys Ser Arg Cys Val Asn Gly Glu Thr
1715            1720                1725

Cys Trp Glu Tyr Pro Ser Asp Leu Cys Asp Pro Arg Thr Trp Asp
1730            1735                1740

Tyr Phe Leu Arg Leu Lys Ala Gly Leu Gly Leu Gln Ile Asp Leu
1745            1750                1755

Ile Val Met Asp Met Glu Val Arg Asp Ser Ser Thr Ser Leu Lys
1760            1765                1770

Ile Glu Thr Asn Val Arg Asn Tyr Val His Arg Ile Leu Asp Glu
1775            1780                1785

Gln Gly Val Leu Ile Tyr Lys Thr Tyr Gly Thr Tyr Ile Cys Glu
1790            1795                1800

Ser Glu Lys Asn Ala Val Thr Ile Leu Gly Pro Met Phe Lys Thr
1805            1810                1815

Val Asp Leu Val Gln Thr Glu Phe Ser Ser Ser Gln Thr Ser Glu
1820            1825                1830

Val Tyr Met Val Cys Lys Gly Leu Lys Lys Leu Ile Asp Glu Pro
1835            1840                1845

Asn Pro Asp Trp Ser Ser Ile Asn Glu Ser Trp Lys Asn Leu Tyr
1850            1855                1860

Ala Phe Gln Ser Ser Glu Gln Glu Phe Ala Arg Ala Lys Lys Val
1865            1870                1875

Ser Thr Tyr Phe Thr Leu Thr Gly Ile Pro Ser Gln Phe Ile Pro
1880            1885                1890

Asp Pro Phe Val Asn Ile Glu Thr Met Leu Gln Ile Phe Gly Val
1895            1900                1905

| | | | | | | | | | | |
|---|---|---|---|---|---|---|---|---|---|---|
|Pro|Thr|Gly|Val|Ser|His|Ala|Ala|Leu|Lys|Ser Ser Asp Arg|
|1910| | | | |1915| | | |1920| |

Pro Ala Asp Leu Leu Thr Ile Ser Leu Phe Tyr Met Ala Ile Ile
1925                1930                1935

Ser Tyr Tyr Asn Ile Asn His Ile Arg Val Gly Pro Ile Pro Pro
1940                1945                1950

Asn Pro Pro Ser Asp Gly Ile Ala Gln Asn Val Gly Ile Ala Ile
1955                1960                1965

Thr Gly Ile Ser Phe Trp Leu Ser Leu Met Glu Lys Asp Ile Pro
1970                1975                1980

Leu Tyr Gln Gln Cys Leu Ala Val Ile Gln Gln Ser Phe Pro Ile
1985                1990                1995

Arg Trp Glu Ala Val Ser Val Lys Gly Gly Tyr Lys Gln Lys Trp
2000                2005                2010

Ser Thr Arg Gly Asp Gly Leu Pro Lys Asp Thr Arg Ile Ser Asp
2015                2020                2025

Ser Leu Ala Pro Ile Gly Asn Trp Ile Arg Ser Leu Glu Leu Val
2030                2035                2040

Arg Asn Gln Val Arg Leu Asn Pro Phe Asn Glu Ile Leu Phe Asn
2045                2050                2055

Gln Leu Cys Arg Thr Val Asp Asn His Leu Lys Trp Ser Asn Leu
2060                2065                2070

Arg Arg Asn Thr Gly Met Ile Glu Trp Ile Asn Arg Arg Ile Ser
2075                2080                2085

Lys Glu Asp Arg Ser Ile Leu Met Leu Lys Ser Asp Leu His Glu
2090                2095                2100

Glu Asn Ser Trp Arg Asp
    2105

<210> SEQ ID NO 8
<211> LENGTH: 11161
<212> TYPE: DNA
<213> ORGANISM: Vesicular stomatitis Indiana virus

<400> SEQUENCE: 8

```
acgaagacaa acaaaccatt attatcatta aaaggctcag gagaaacttt aacagtaatc    60
aaaatgtctg ttacagtcaa gagaatcatt gacaacacag tcatagttcc aaaacttcct   120
gcaaatgagg atccagtgga atacccggca gattacttca aaaatcaaa ggagattcct   180 ctttacatca atactacaaa aagtttgtca gatctaagag atatgtcta ccaaggcctc   240 aaatccggaa atgtatcaat catacatgtc aacagctact gtatggagc attgaaggac   300 atccggggta gttggataaa agattggtca agtttcggaa taaacatcgg aaggcaggg   360 gatacaatcg gaatatttga ccttgtatcc ttgaaagccc tggacggtgt acttccagat   420
ggagtatcgg atgcttccag aaccagcgca gatgacaaat ggttgccttt gtatctactt   480
ggcttataca gagtgggcag aacacaaatg cctgaataca gaaaaaggct catggatggg   540
ctgacaaatc aatgcaaaat gatcaatgaa cagtttgaac ctcttgtgcc agaaggtcgt   600
gacatttttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca catttggac acctctgcaa ataaccgga   780 atgtctacag aagatgtgac gacctggatc ttgaaccgag aagttgcaga tgagatggtc   840
caaatgatgc ttccaggcca agaaattgac aaggctgatt catacatgcc ttatttgatc   900
```

```
gactttggat tgtcttctaa gtctccatat tcttccgtca aaaacccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgctg acttggcaca acagttttgt gttggagata gcaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaacga   1260
gcagtcatgt cactgcaagg cctaagagag aagacaattg caagtatgc taagtcagag    1320
tttgacaaat gaccctataa ttctcagatc acctattata tattatgcta catatgaaaa   1380
aaactaacag atatcatgga taatctcaca aaagttcgtg agtatctcaa gtcctattct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga acagcctga gcttgaatcc    1740
gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaagcgcca gataactccg    1920
gatgtatata aggtcactcc agtgatgaac acacatccgt accaatcaga agccgtatca   1980
gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taaagaggcc atcctgctcg gtctgaggta caaaaagttg   2160
tacaatcagg cgagagtcaa atattctctg tagactatga aaaaagtaa cagatatcac    2220
aatctaagtg ttatcccaat ccattcatca tgagttcctt aaagaagatt ctcggtctga   2280
aggggaaagg taagaaatct aagaaattag ggatcgcacc accccttat gaagaggaca    2340
ctaacatgga gtatgctccg agcgctccaa ttgacaaatc ctattttgga gttgacgaga   2400
tggacactca tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaagatc ttggcttttt   2580
tgggttcttc taatctaaag gccactccag cggtattggc agatcaaggt caaccagagt   2640
atcatgctca ctgtgaaggc agggcttatt tgccacacag aatggggaag accccctccca  2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcttggg tcctggattc tgtcagccac ttcaaatgag   2940
ctagtctagc ttccagcttc tgaacaatcc ccggtttact cagtctctcc taattccagc   3000
ctttcgaaca actaatatcc tgtcttctct atcccgatga aaaaaactaa cagagatcga   3060
tctgtttcct tgacaccatg aagtgccttt tgtacttagc tttttttattc atcggggtga   3120
attgcaagtt caccatagtt tttccacaca accaaaaagg aaactggaaa atgttccttt   3180
ccaattacca ttattgcccg tcaagctcag atttaaattg gcataatgac ttagtaggca   3240
```

```
cagccttaca agtcaaaatg cccaagagtc acaaggctat tcaagcagac ggttggatgt    3300
gtcatgcttc caaatgggtc actacttgtg atttccgctg gtacggaccg aagtatataa    3360
cacattccat ccgatccttc actccatctg tagaacaatg caaggaaagc attgaacaaa    3420
cgaaacaagg aacttggctg aatccaggct tccctcctca agttgtggaa tatgcaactg    3480
tgacggatgc tgaagcagcg attgtccagg tgactcctca ccatgtgctt gttgatgaat    3540
acacaggaga atgggttgat tcacagttca tcaacggaaa atgcagcaat gacatatgcc    3600
ccactgtcca taactccaca acctggcatt ccgactataa ggtcaaaggg ctatgtgatt    3660
ctaacctcat ttccatggac atcaccttct tctcagagga cggagagcta tcatccctag    3720
gaaagaaggg cacagggttc agaagtaact actttgctta tgaaactgga gacaaggcct    3780
gcaaaatgca gtactgcaag cattggggag tcagactccc atcaggtgtc tggttcgaga    3840
tggctgataa ggmtctcttt gctgcagcca gattccctga tgcccagaa gggtcaagta    3900 tctctgctcc atctcagacc tcagtggatg taagtctcat tcaggacgtt gagaggatct    3960
tggattattc cctctgccaa gaaacctgga gcaaaatcag agcgggtctt cccatctctc    4020
cagtggatct cagctatctt gctcctaaaa acccaggaac cggtcctgtc tttaccataa    4080
tcaatggtac cctaaaatac tttgagacca gatacatcag agtcgatatt gctgctccaa    4140
tcctctcaag aatggtcgga atgatcagtg aactaccac agaaagggta ctgtgggatg    4200
actgggctcc atatgaagac gtggaaattg acccaatgg agttctgagg accagttcag    4260
gatataagtt tcctttatat atgattggac atggtatgtt ggactccgat cttcatctta    4320
gctcaaaggc tcaggtgttt gaacatcctc acattcaaga cgctgcttcg cagcttcctg    4380
atggtgagac tttattttt ggtgatactg ggctatccaa aaatccaatc gagtttgtag    4440
aaggttggtt cagtagttgg aagagctcta ttgcctctt tttctttacc ataggggttaa    4500 tcattggact attcttggtt ctccgagttg gtatttatct ttgcattaaa ttaaagcaca    4560
ccaagaaaag acagatttat acagacatag agatgaaccg acttggaaag taactcaaat    4620
cctgcacaac agattcttca tgtttgaacc aaatcaactt gtgatatcat gctcaaagag    4680
gccttaatta tattttaatt tttaattttt atgaaaaaaa ctaacagcaa tcatggaagt    4740
ccacgatttt gagaccgacg agttcaatga tttcaatgaa gatgactatg ccacaagaga    4800
attcctgaat cccgatgagc gcatgacgta cttgaatcat gctgattaca atttgaattc    4860
tcctctaatt agtgatgata ttgacaattt gatcaggaaa ttcaattctc ttccgattcc    4920
ctcgatgtgg gatagtaaga actgggatgg agttcttgag atgttaacat catgtcaagc    4980
caatcccatc tcaacatctc agatgcataa atggatggga agttggttaa tgtctgataa    5040
tcatgatgcc agtcaagggt atagttttt acatgaagtg gacaaagagg cagaaataac    5100
atttgacgtg gtggagacct tcatccgcgg ctggggcaac aaaccaattg aatacatcaa    5160
aaaggaaaga tggactgact cattcaaaat tctcgcttat ttgtgtcaaa gttttttgga    5220
cttacacaag ttgacattaa tcttaaatgc tgtctctgag gtggaattgc tcaacttggc    5280
gaggactttc aaaggcaaag tcagaagaag ttctcatgga acgaacatat gcaggattag    5340
ggttcccagc ttgggtccta cttttatttc agaaggatgg gcttacttca agaaacttga    5400
tattctaatg gaccgaaact ttctgttaat ggtcaaagat gtgattatag ggaggatgca    5460
aacggtgcta tccatggtat gtagaataga caacctgttc tcagagcaag acatcttctc    5520
ccttctaaat atctacagaa ttggagataa aattgtggag aggcagggaa attttcttta    5580
tgacttgatt aaaatggtgg aaccgatatg caacttgaag ctgatgaaat tagcaagaga    5640
```

```
atcaaggcct ttagtcccac aattccctca ttttgaaaat catatcaaga cttctgttga    5700
tgaaggggca aaaattgacc gaggtataag attcctccat gatcagataa tgagtgtgaa    5760
aacagtggat ctcacactgg tgatttatgg atcgttcaga cattggggtc atccttttat    5820
agattattac actggactag aaaaattaca ttcccaagta accatgaaga aagatattga    5880
tgtgtcatat gcaaaagcac ttgcaagtga tttagctcgg attgttctat ttcaacagtt    5940
caatgatcat aaaaagtggt tcgtgaatgg agacttgctc cctcatgatc atccctttaa    6000
aagtcatgtt aaagaaaata catggcctac agctgctcaa gttcaagatt tggagataa     6060 atggcatgaa cttccgctga ttaaatgttt tgaaataccc gacttactag acccatcgat    6120
aatatactct gacaaaagtc attcaatgaa taggtcagag gtgttgaaac atgtccgaat    6180
gaatccgaac actcctatcc ctagtaaaaa ggtgttgcag actatgttgg acacaaaggc    6240
taccaattgg aaagaatttc ttaaagagat tgatgagaag ggcttagatg atgatgatct    6300
aattattggt cttaaaggaa aggagaggga actgaagttg gcaggtagat ttttctccct    6360
aatgtcttgg aaattgcgag aatactttgt aattaccgaa tatttgataa agactcattt    6420
cgtccctatg tttaaaggcc tgacaatggc ggacgatcta actgcagtca ttaaaaagat    6480
gttagattcc tcatccggcc aaggattgaa gtcatatgag gcaatttgca tagccaatca    6540
cattgattac gaaaaatgga ataaccacca aggaagtta tcaaacggcc cagtgttccg     6600
agttatgggc cagttcttag gttatccatc cttaatcgag agaactcatg aattttttga    6660
gaaaagtctt atatactaca atggaagacc agacttgatg cgtgttcaca acaacacact    6720
gatcaattca acctcccaac gagtttgttg gcaaggacaa gagggtggac tggaaggtct    6780
acggcaaaaa ggatggagta tcctcaatct actggttatt caagagagg ctaaaatcag     6840 aaacactgct gtcaaagtct tggcacaagg tgataatcaa gttatttgca cacagtataa    6900
aacgaagaaa tcgagaaacg ttgtagaatt acagggtgct ctcaatcaaa tggtttctaa    6960
taatgagaaa attatgactg caatcaaaat agggacaggg aagttaggac ttttgataaa    7020
tgacgatgag actatgcaat ctgcagatta cttgaattat ggaaaaatac cgattttccg    7080
tggagtgatt agagggttag agaccaagag atggtcacga gtgacttgtg tcaccaatga    7140
ccaaataccc acttgtgcta atataatgag ctcagtttcc acaaatgctc tcaccgtagc    7200
tcattttgct gagaacccaa tcaatgccat gatacagtac aattattttg ggacatttgc    7260
tagactcttg ttgatgatgc atgatcctgc tcttcgtcaa tcattgtatg aagttcaaga    7320
taagataccg ggcttgcaca gttctacttt caaatacgcc atgttgtatt ggacccttc     7380 cattggagga gtgtcgggca tgtctttgtc caggtttttg attagagcct tcccagatcc    7440
cgtaacagaa agtctctcat tctggagatt catccatgta catgctcgaa gtgagcatct    7500
gaaggagatg agtgcagtat ttggaaaccc cgagatagcc aagtttcgaa taactcacat    7560
agacaagcta gtagaagatc caacctctct gaacatcgct atgggaatga gtccagcgaa    7620
cttgttaaag actgaggtta aaaaatgctt aatcgaatca agacaaacca tcaggaacca    7680
ggtgattaag gatgcaacca tatatttgta tcatgaagag gatcggctca gaagtttctt    7740
atggtcaata aatcctctgt tcactagatt tttaagtgaa ttcaaatcag gcactttttt    7800
gggagtcgca gacgggctca tcagtctatt tcaaaattct cgtactattc ggaactcctt    7860
taagaaaaag tatcataggg aattggatga tttgattgtg aggagtgagg atcctcttt     7920 gacacattta gggaaacttc atttgagaag gggatcatgt aaaatgtgga catgttcagc    7980
```

```
tactcatgct gacacattaa gatacaaatc ctggggccgt acagttattg ggacaactgt   8040
accccatcca ttagaaatgt tgggtccaca acatcgaaaa gagactcctt gtgcaccatg   8100
taacacatca gggttcaatt atgtttctgt gcattgtcca gacgggatcc atgacgtctt   8160
tagttcacgg ggaccattgc ctgcttatct agggtctaaa acatctgaat ctacatctat   8220
tttgcagcct tgggaaaggg aaagcaaagt cccactgatt aaaagagcta cacgtcttag   8280
agatgctatc tcttggtttg ttgaacccga ctctaaacta gcaatgacta tactttctaa   8340
catccactct ttaacaggcg aagaatggac caaaaggcag catgggttca aaagaacagg   8400
gtctgccctt cataggtttt cgacatctcg gatgagccat ggtgggttcg catctcagag   8460
cactgcagca ttgaccaggt tgatggcaac tacagacacc atgagggatc tgggagatca   8520
gaatttcgac tttttattcc aagcaacgtt gctctatgct caaattacca ccactgttgc   8580
aagagacgga tggatcacca gttgtacaga tcattatcat attgcctgta agtcctgttt   8640
gagacccata aagagatca ccctggactc aagtatggac tacacgcccc cagatgtatc   8700
ccatgtgctg aagacatgga ggaatgggga aggttcgtgg ggacaagaga taaaacagat   8760
ctatccttta aagggaatt ggaagaattt agcacctgct gagcaatcct atcaagtcgg   8820
cagatgtata ggttttctat atggagactt ggcgtataga aaatctactc atgccgagga   8880
cagttctcta tttcctctat ctatacaagg tcgtattaga ggtcgaggtt tcttaaaagg   8940
gttgctagac ggattaatga gagcaagttg ctgccaagta atacaccgga gaagtctggc   9000
tcatttgaag aggccggcca acgcagtgta cggaggtttg atttacttga ttgataaatt   9060
gagtgtatca cctccattcc tttctcttac tagatcagga cctattagag acgaattaga   9120
aacgattccc cacaagatcc caacctccta tccgacaagc aaccgtgata tgggggtgat   9180
tgtcagaaat tacttcaaat accaatgccg tctaattgaa aagggaaaat acagatcaca   9240
ttattcacaa ttatggttat tctcagatgt cttatccata gacttcattg gaccattctc   9300
tatttccacc ccctcttgc aaatcctata caagccattt ttatctggga agataagaa   9360 tgagttgaga gagctggcaa atctttcttc attgctaaga tcaggagagg ggtgggaaga   9420
catacatgtg aaattcttca ccaaggacat attattgtgt ccagaggaaa tcagacatgc   9480
ttgcaagttc gggattgcta aggataataa taaagacatg agctatcccc cttggggaag   9540
ggaatccaga gggacaatta caacaatccc tgtttattat acgaccaccc cttacccaaa   9600
gatgctagag atgcctccaa gaatccaaaa tcccctgctg tccggaatca ggttgggcca   9660
attaccaact ggcgctcatt ataaaattcg gagtatatta catggaatgg gaatccatta   9720
cagggacttc ttgagttgtg gagacggctc cggagggatg actgctgcat tactacgaga   9780
aaatgtgcat agcagaggaa tattcaatag tctgttagaa ttatcagggt cagtcatgcg   9840
aggcgcctct cctgagcccc ccagtgccct agaaacttta ggaggagata aatcgagatg   9900
tgtaaatggt gaaacatgtt gggaatatcc atctgactta tgtgacccaa ggacttggga   9960
ctatttcctc cgactcaaag caggcttggg gcttcaaatt gatttaattg taatggatat  10020
ggaagttcgg gattcttcta ctagcctgaa aattgagacg aatgttagaa attatgtgca  10080
ccggattttg gatgagcaag gagttttaat ctacaagact tatggaacat atatttgtga  10140
gagcgaaaag aatgcagtaa caatccttgg tcccatgttc aagacggtcg acttagttca  10200
aacagaattt agtagttctc aaacgtctga agtatatatg gtatgtaaag gtttgaagaa  10260
attaatcgat gaacccaatc ccgattggtc ttccatcaat gaatcctgga aaacctgta   10320 cgcattccag tcatcagaac aggaatttgc cagagcaaag aaggttagta catactttac  10380
```

| | |
|---|---|
| cttgacaggt attccctccc aattcattcc tgatccttt gtaaacattg agactatgct | 10440 |
| acaaatattc ggagtaccca cgggtgtgtc tcatgcggct gccttaaaat catctgatag | 10500 |
| acctgcagat ttattgacca ttagccttt ttatatggcg attatatcgt attataacat | 10560 |
| caatcatatc agagtaggac cgatacctcc gaaccccca tcagatggaa ttgcacaaaa | 10620 |
| tgtggggatc gctataactg gtataagctt ttggctgagt ttgatggaga agacattcc | 10680 |
| actatatcaa cagtgtttag cagttatcca gcaatcattc ccgattaggt gggaggctgt | 10740 |
| ttcagtaaaa ggaggataca agcagaagtg gagtactaga ggtgatgggc tcccaaaaga | 10800 |
| tacccgaatt tcagactcct tggccccaat cgggaactgg atcagatctc tggaattggt | 10860 |
| ccgaaaccaa gttcgtctaa atccattcaa tgagatcttg ttcaatcagc tatgtcgtac | 10920 |
| agtggataat catttgaaat ggtcaaattt gcgaagaaac acaggaatga ttgaatggat | 10980 |
| caatagacga atttcaaaag aagaccggtc tatactgatg ttgaagagtg acctacacga | 11040 |
| ggaaaactct tggagagatt aaaaaatcat gaggagactc caaactttaa gtatgaaaaa | 11100 |
| aactttgatc cttaagaccc tcttgtggtt tttatttttt atctggtttt gtggtcttcg | 11160 |
| t | 11161 |

<210> SEQ ID NO 9
<211> LENGTH: 1489
<212> TYPE: DNA
<213> ORGANISM: Vesicular stomatitis indiana virus

<400> SEQUENCE: 9

| | |
|---|---|
| atagtcgaga cgacgaagac aaacaaacca ttattatcat taaaaggctc aggagaaact | 60 |
| ttaacagtaa tcaaaatgtc tgttacagtc aagagaatca ttgacaacac agtcatagtt | 120 |
| ccaaaacttc ctgcaaatga ggatccagtg gaatacccgg cagattactt cagaaaatca | 180 |
| aaggagattc ctctttacat caatactaca aaaagtttgt cagatctaag aggatatgtc | 240 |
| taccaaggcc tcaaatccgg aaatgtatca atcatacatg tcaacagcta cttgtatgga | 300 |
| gcattgaagg acatccgggg taagttggat aaagattggt caagtttcgg aataaacatc | 360 |
| gggaaggcag gggatacaat cggaatattt gaccttgtat ccttgaaagc cctggacggt | 420 |
| gtacttccag atggagtatc ggatgcttcc agaaccagcg cagatgacaa atggttgcct | 480 |
| ttgtatctac ttggcttata cagagtgggc agaacacaaa tgcctgaata cagaaaaagg | 540 |
| ctcatggatg ggctgacaaa tcaatgcaaa atgatcaatg aacagtttga acctcttgtg | 600 |
| ccagaaggtc gtgacatttt tgatgtgtgg ggaaatgaca gtaattacac aaaaattgtc | 660 |
| gctgcagtgg acatgttctt ccacatgttc aaaaaacatg aatgtgcctc gttcagatac | 720 |
| ggaactattg tttccagatt caagattgt gctgcattgg caacatttgg acacctctgc | 780 |
| aaaataaccg gaatgtctac agaagatgtg acgacctgga tcttgaaccg agaagttgca | 840 |
| gatgagatgg tccaaatgat gcttccaggc caagaaattg acaaggctga ttcatacatg | 900 |
| ccttatttga tcgactttgg attgtcttct aagtctccat attcttccgt caaaaaccct | 960 |
| gccttccact ctgggggca attgacagct cttctgctca gatccaccag agcaaggaat | 1020 |
| gcccgacagc tgatgacat tgagtataca tctcttacta cagcaggttt gttgtacgct | 1080 |
| tatgcagtag atcctctgc tgacttggca acagttttt gtgttggaga tagcaaatac | 1140 |
| actccagatg atagtaccgg aggattgacg actaatgcac cgccacaagg cagagatgtg | 1200 |
| gtcgaatggc tcggatggtt tgaagatcaa aacagaaaac cgactcctga tatgatgcag | 1260 |

```
tatgcgaaac gagcagtcat gtcactgcaa ggcctaagag agaagacaat tggcaagtat      1320
gctaagtcag agtttgacaa atgaccctat aattctcaga tcacctatta tatattatgc      1380
tagcttgttc gaactcttaa ttaacgcccc gagtatgtcg acgtacttaa gaccctcttg      1440 tggttttat tttttatctg gttttgtggt cttcgtcgtc tccggccgg                    1489

<210> SEQ ID NO 10
<211> LENGTH: 1645
<212> TYPE: DNA
<213> ORGANISM: Vesicular stomatitis indiana virus

<400> SEQUENCE: 10
gctagctatg aaaaaaacta acagatatca tggataatct cacaaaagtt cgtgagtatc        60
tcaagtccta ttctcgtcta gatcaggcgg taggagagat agatgagatc gaagcacaac       120
gagctgaaaa gtccaattat gagttgttcc aagaggacgg agtggaagag catactaggc       180
cctcttattt tcaggcagca gatgattctc acacagaatc tgaaccagaa attgaagaca       240
atcaaggctt gtatgtacca gatccggaag ctgagcaagt tgaaggcttt atacaggggc       300
ctttagatga ctatgcagat gaggacgtgg atgttgtatt cacttcggac tggaaacagc       360
ctgagcttga atccgacgag catggaaaga ccttacggtt gacattgcca gagggtttaa       420
gtggagagca gaaatcccag tggcttttga cgattaaagc agtcgttcaa gtgccaaac       480 actggaatct ggcagagtgc acatttgaag catcgggaga aggggtcatc ataaaaaagc       540
gccagataac tccggatgta tataaggtca ctccagtgat gaacacacat ccgtcccaat       600
cagaagccgt atcagatgtt tggtctctct caaagacatc catgacttc caacccaaga       660 aagcaagtct tcagcctctc accatatcct tggatgaatt gttctcatct agaggagaat       720
tcatctctgt cggaggtaac ggacgaatgt ctcataaaga ggccatcctg ctcggtctga       780
ggtacaaaaa gttgtacaat caggcgagag tcaaatattc tctgtagact agtatgaaaa       840
aaagtaacag atatcacaat ctaagtgtta tcccaatcca ttcatcatga gttccttaaa       900
gaagattctc ggtctgaagg ggaaaggtaa gaaatctaag aaattaggga tcgcaccacc       960
cccttatgaa gaggacacta acatggagta tgctccgagc gctccaattg acaaatccta      1020
ttttggagtt gacgagatgg acactcatga tccgaatcaa ttaagatatg agaaattctt      1080
ctttacagtg aaaatgacgg ttagatctaa tcgtccgttc agaacatact cagatgtggc      1140
agccgctgta tcccattggg atcacatgta catcggaatg gcagggaaac gtcccttcta      1200
caagatcttg gcttttttgg ttcttctaa tctaaaggcc actccagcgg tattggcaga      1260
tcaaggtcaa ccagagtatc atgctcactg tgaaggcagg gcttatttgc cacacagaat      1320
ggggaagacc cctcccatgc tcaatgtacc agagcacttc agaagaccat caatataggg     1380
tctttacaag ggaacgattg agctcacaat gaccatctac gatgatgagt cactggaagc      1440
agctcctatg atctgggatc atttcaattc ttccaaattt tctgatttca gagagaaggc      1500
cttaatgttt ggcctgattg tcgagaaaaa ggcatctgga gcttgggtcc tggattctgt      1560
cagccacttc aaaatgagcta gtctagcttc cagcttctga caatccccg gtttactcag      1620 tctctcctaa ttccagcctt tcgaa                                            1645

<210> SEQ ID NO 11
<211> LENGTH: 1645
<212> TYPE: DNA
<213> ORGANISM: Vesicular stomatitis indiana virus

<400> SEQUENCE: 11
```

```
gctagctatg aaaaaaacta acagatatca tggataatct cacaaaagtt cgtgagtatc        60
tcaagtccta ttctcgtcta gatcaggcgg taggagagat agatgagatc gaagcacaac       120
gagctgaaaa gtccaattat gagttgttcc aagaggacgg agtggaagag catactaggc       180
cctcttattt tcaggcagca gatgattctg acacagaatc tgaaccagaa attgaagaca       240
atcaaggctt gtatgtacca gatccggaag ctgagcaagt tgaaggcttt atacaggggc       300
ctttagatga ctatgcagat gaggacgtgg atgttgtatt cacttcggac tggaaacagc       360
ctgagcttga atccgacgag catggaaaga ccttacggtt gacattgcca gagggtttaa       420
gtggagagca gaaatcccag tggcttttga cgattaaagc agtcgttcaa agtgccaaac       480
actggaatct ggcagagtgc acatttgaag catcgggaga aggggtcatc ataaaaaagc       540
gccagataac tccggatgta tataaggtca ctccagtgat gaacacacat ccgtcccaat       600
cagaagccgt atcagatgtt tggtctctct caaagacatc catgactttc caacccaaga       660
aagcaagtct tcagcctctc accatatcct tggatgaatt gttctcatct agaggagaat       720
tcatctctgt cggaggtaac ggacgaatgt ctcataaaga ggccatcctg ctcggtctga       780
ggtacaaaaa gttgtacaat caggcgagag tcaaatattc tctgtagact agtatgaaaa       840
aaagtaacag atatcacaat ctaagtgtta tcccaatcca ttcatcatga gttccttaaa       900
gaagattctc ggtctgaagg ggaaaggtaa gaaatctaag aaattaggga tcgcaccacc       960
cccttatgaa gaggacacta acatggagta tgctccgagc gctccaattg acaaatccta      1020
ttttggagtt gacgagatgg acactcatga tccgaatcaa ttaagatatg agaaattctt      1080
ctttacagtg aaaatgacgg ttagatctaa tcgtccgttc agaacatact cagatgtggc      1140
agccgctgta tcccattggg atcacatgta catcggaatg gcagggaaac gtcccttcta      1200
caagatcttg gcttttttgg gttcttctaa tctaaaggcc actccagcgg tattggcaga      1260
tcaaggtcaa ccagagtatc atgctcactg tgaaggcagg gcttatttgc cacacagaat      1320
ggggaagacc cctcccatgc tcaatgtacc agagcacttc agaagaccat tcaatatagg      1380
tctttacaag ggaacgattg agctcacaat gaccatctac gatgatgagt cactggaagc      1440
agctcctatg atctgggatc atttcaattc ttccaaattt tctgatttca gagagaaggc      1500
cttaatgttt ggcctgattg tcgagaaaaa ggcatctgga gcttgggtcc tggattctgt      1560
cagccacttc aaatgagcta gtctagcttc agcttctga caatccccg gtttactcag       1620 tctctcctaa ttccagcctt tcgaa                                            1645
```

<210> SEQ ID NO 12
<211> LENGTH: 2851
<212> TYPE: DNA
<213> ORGANISM: Vesicular stomatitis indiana virus

<400> SEQUENCE: 12

```
ttaattaaat tttaatttt aattttatg aaaaaaacta acagcaatca tggaagtcca        60
cgattttgag accgacgagt tcaatgattt caatgaagat gactatgcca aagagaatt       120 cctgaatccc gatgagcgca tgacgtactt gaatcatgct gattacaatt tgaattctcc       180
tctaattagt gatgatattg acaatttgat caggaaattc aattctcttc cgattccctc       240
gatgtgggat agtaagaact gggatggagt tcttgagatg ttaacatcat gtcaagccaa       300
tcccatctca acatctcaga tgcataaatg gatgggaagt tggttaatgt ctgataatca       360
tgatgccagt caagggtata gttttttaca tgaagtggac aaagaggcag aaataacatt       420
```

```
tgacgtggtg gagaccttca tccgcggctg gggcaacaaa ccaattgaat acatcaaaaa    480
ggaaagatgg actgactcat tcaaaattct cgcttatttg tgtcaaaagt ttttggactt    540
acacaagttg acattaatct taaatgctgt ctctgaggtg gaattgctca acttggcgag    600
gactttcaaa ggcaaagtca gaagaagttc tcatggaacg aacatatgca ggcttagggt    660
tcccagcttg ggtcctactt ttatttcaga aggatgggct tacttcaaga aacttgatat    720
tctaatggac cgaaactttc tgttaatggt caaagatgtg attataggga ggatgcaaac    780
ggtgctatcc atggtatgta gaatagacaa cctgttctca gagcaagaca tcttctccct    840
tctaaatatc tacagaattg gagataaaat tgtggagagg cagggaaatt tttcttatga    900
cttgattaaa atggtggaac cgatatgcaa cttgaagctg atgaaattag caagagaatc    960
aaggccttta gtcccacaat tccctcattt tgaaaatcat atcaagactt ctgttgatga   1020
aggggcaaaa attgaccgag gtataagatt cctccatgat cagataatga gtgtgaaaac   1080
agtggatctc acactggtga tttatggatc gttcagacat tggggtcatc cttttataga   1140
ttattacgct ggactagaaa aattacattc ccaagtaacc atgaagaaag atattgatgt   1200
gtcatatgca aaagcacttg caagtgattt agctcggatt gttctatttc aacagttcaa   1260
tgatcataaa aagtggttcg tgaatggaga cttgctccct catgatcatc cctttaaaag   1320
tcatgttaaa gaaaatacat ggcctacagc tgctcaagtt caagattttg gagataaatg   1380
gcatgaactt ccgctgatta aatgttttga aatacccgac ttactagacc catcgataat   1440
atactctgac aaaagtcatt caatgaatag gtcagaggtg ttgaaacatg tccgaatgaa   1500
tccgaacact cctatcccta gtaaaaaggt gttgcagact atgttggaca caaaggctac   1560
caattggaaa gaatttctta agagattga tgagaagggc ttagatgatg atgatctaat   1620
tattggtctt aaaggaaagg agagggaact gaagttggca ggtagatttt tctcccctaat   1680 gtcttggaaa ttgcgagaat actttgtaat taccgaatat ttgataaaga ctcatttcgt   1740
ccctatgttt aaaggcctga caatggcgga cgatcaact gcagtcatta aaaagatgtt   1800
agattcctca tccggccaag gattgaagtc atatgaggca atttgcatag ccaatcacat   1860
tgattacgaa aaatgaata accaccaaag gaagttatca aacggcccag tgttccgagt   1920
tatgggccag ttcttaggtt atccatcctt aatcgagaga actcatgaat ttttttgagaa   1980 aagtctttata tactacaatg gaagaccaga cttgatgcgt gttcacaaca acacactgat   2040
caattcaacc tcccaacgag tttgttggca aggacaagag ggtggactgg aaggtctacg   2100
gcaaaaagga tggagtatcc tcaatctact ggttattcaa agagaggcta aaatcagaaa   2160
cactgctgtc aaagtcttgg cacaaggtga taatcaagtt atttgcacac agtataaaac   2220
gaagaaatcg agaaacgttg tagaattaca gggtgctctc aatcaaatgg tttctaataa   2280
tgagaaaatt atgactgcaa tcaaaatagg gacagggaag ttaggacttt tgataaatga   2340
cgatgagact atgcaatctg cagattactt gaattatgga aaaataccga ttttccgtgg   2400
agtgattaga gggttagaga ccaagagatg gtcacgagtg acttgtgtca ccaatgacca   2460
aatacccact tgtgctaata taatgagctc agtttccaca aatgctctca ccgtagctca   2520
ttttgctgag aacccaatca atgccatgat acagtacaat tattttggga catttgctag   2580
actcttgttg atgatgcatg atcctgctct tcgtcaatca ttgtatgaag ttcaagataa   2640
gataccgggc ttgcacagtt ctactttcaa atacgccatg ttgtatttgg accccttccat   2700 tggaggagtc tcgggcatgt cttttgtccag gttttttgatt agagccttcc cagatcccgt   2760
aacagaaagt ctctcattct ggagattcat ccatgtacat gctcgaagtg agcatctgaa   2820
```

-continued ggagatgagt gcagtatttg aaacccccga g                                           2851

<210> SEQ ID NO 13
<211> LENGTH: 2664
<212> TYPE: DNA
<213> ORGANISM: Vesicular stomatitis indiana virus

<400> SEQUENCE: 13

| cccgagatag ccaagttccg aataactcac atagacaagc tagtagaaga tccaacctct | 60 |
| ctgaacatcg ctatgggaat gagtccagcg aacttgttaa agactgaggt taaaaaatgc | 120 |
| ttaatcgaat caagacaaac catcaggaac caggtgatta aggatgcaac catatatttg | 180 |
| tatcatgaag aggatcggct cagaagtttc ttatggtcaa taaatcctct gttccctaga | 240 |
| ttttaagtg aattcaaatc aggcactttt tggggagtcg cagacgggct catcagtcta | 300 |
| tttcaaaatt ctcgtactat tcggaactcc tttaagaaaa agtatcatag ggaattggat | 360 |
| gatttgattg tgaggagtga ggtatcctct ttgacacatt tagggaaact tcatttgaga | 420 |
| aggggatcat gtaaaatgtg gacatgttca gctactcatg ctgacacatt aagatacaaa | 480 |
| tcctggggcc gtacagttat tgggacaact gtacccccatc cattagaaat gttgggtcca | 540 |
| caacatcgaa aagagactcc ttgtgcacca tgtaacacat caggggttcaa ttatgtttct | 600 |
| gtgcattgtc cagacgggat ccatgacgtc tttagttcac ggggaccatt gcctgcttat | 660 |
| ctagggtcta aacatctga atctacatct attttgcagc cttgggaaag ggaaagcaaa | 720 |
| gtcccactga ttaaaagagc tacacgtctt agagatgcta tctcttggtt tgttgaaccc | 780 |
| gactctaaac tagcaatgac tatactttct aacatccact ctttaacagg cgaagaatgg | 840 |
| accaaaaggc agcatgggtt caaaagaaca gggtctgccc ttcataggtt ttcgacatct | 900 |
| cggatgagcc atggtgggtt cgcatctcag agcactgcag cattgaccag gttgatggca | 960 |
| actacagaca ccatgaggga tctgggagat cagaatttcg acttttatt ccaagcaacg | 1020 |
| ttgctctatg ctcaaattac caccactgtt gcaagagacg gatggatcac cagttgtaca | 1080 |
| gatcattatc atattgcctg taagtcctgt ttgagaccca tagaagagat caccctggac | 1140 |
| tcaagtatgg actacacgcc cccagatgta tcccatgtgc tgaagacatg gaggaatggg | 1200 |
| gaaggttcgt ggggacaaga gataaaacag atctatcctt tagaagggaa ttggaagaat | 1260 |
| ttagcacctg ctgagcaatc ctatcaagtc ggcagatgta taggttttct atatggagac | 1320 |
| ttggcgtata gaaaatctac tcatgccgag acagttctc tatttcctct atctatacaa | 1380 |
| ggtcgtatta gaggtcgagg tttcttaaaa gggttgctag acggattaat gagagcaagt | 1440 |
| tgctgccaag taatacaccg gagaagtctg gctcatttga agaggccggc caacgcagtg | 1500 |
| tacgaaggtt tgatttactt gattgataaa ttgagtgtat cacctccatt cctttctctt | 1560 |
| actagatcag gacctattag agacgaatta gaaacgattc cccacaagat cccaacctcc | 1620 |
| tatccgacaa gcaaccgtga tatggggtg attgtcagaa attacttcaa ataccaatgc | 1680 |
| cgtctaattg aaaagggaaa atacagatca cattattcac aattatggtt attctcagat | 1740 |
| gtcttatcca tagacttcat tggaccattc tctatttcca ccaccctctt gcaaatccta | 1800 |
| tacaagccat ttttatctgg aaagataag aatgagttga gagctggc aaatctttct | 1860 |
| tcattgctaa gatcaggaga ggggtgggaa gacatacatg tgaaattctt caccaaggac | 1920 |
| atattattgt gtccagagga aatcagacat gcttgcaagt tcgggattgc taaggataat | 1980 |
| aataaagaca tgagctatcc ccccttgggga agggaatcca gagggacaat tacaacaatc | 2040 |

```
cctgtttatt atacgaccac cccttaccca aagatgctag agatgcctcc aagaatccaa    2100
aatcccctgc tgtccggaat caggttgggc caattaccaa ctggcgctca ttataaaatt    2160
cggagtatat tacatggaat gggaatccat tacagggact tcttgagttg tggagacggc    2220
tccggaggga tgactgctgc attactacga gaaaatgtgc atagcagagg aatattcaat    2280
agtctgttag aattatcagg gtcagtcatg cgaggcgcct ctcctgagcc ccccagtgcc    2340
ctagaaactt taggaggaga taaatcgaga tgtgtaaatg gtgaaacatg ttgggaatat    2400
ccatctgact tatgtgaccc aaggacttgg gactatttcc tccgactcaa agcaggcttg    2460
gggcttcaaa ttgatttaat tgtaatggat atggaagttc gggattcttc tactagcctg    2520
aaaattgaga cgaatgttag aaattatgtg caccggattt tggatgagca aggagtttta    2580
atctacaaga cttatggaac atatatttgt gagagcgaaa agaatgcagt aacaatcctt    2640
ggtcccatgt tcaagacggt cgac                                           2664

<210> SEQ ID NO 14
<211> LENGTH: 930
<212> TYPE: DNA
<213> ORGANISM: Vesicular stomatitis indiana virus

<400> SEQUENCE: 14
gtcgacttag ttcaaacaga atttagtagt tctcaaacgt ctgaagtata tatggtatgt      60
aaaggtttga agaaattaat cgatgaaccc aatcccgatt ggtcttccat caatgaatcc     120
tggaaaaacc tgtacgcatt ccagtcatca gaacaggaat tgccagagc aaagaaggtt     180 agtacatact ttaccttgac aggtattccc tcccaattca ttcctgatcc ttttgtaaac     240
attgagacta tgctacaaat attcggagta cccacgggtg tgtctcatgc ggctgcctta     300
aaatcatctg atagacctgc agatttattg accattagcc ttttttatat ggcgattata     360
tcgtattata acatcaatca tatcagagta ggaccgatac ctccgaaccc cccatcagat     420
ggaattgcac aaaatgtggg gatcgctata actggtataa gcttttggct gagtttgatg     480
gagaaagaca ttccactata tcaacagtgt ttagcagtta ccagcaatc attcccgatt     540 aggtgggagg ctgtttcagt aaaaggagga tacaagcaga agtggagtac tagaggtgat     600
gggctcccaa aagataccc aatttcagac tccttggccc aatcgggaa ctggatcaga     660 tctctggaat tggtccgaaa ccaagttcgt ctaaatccat tcaatgagat cttgttcaat     720
cagctatgtc gtacagtgga taatcatttg aaatggtcaa atttgcgaaa aaacacagga     780
atgattgaat ggatcaatag acgaatttca aaagaagacc ggtctatact gatgttgaag     840
agtgacctac acgaggaaaa ctcttggaga gattaaaaaa tcatgaggag actccaaact     900
ttaagtatga aaaaactttt gatccttaag                                      930

<210> SEQ ID NO 15
<211> LENGTH: 23
<212> TYPE: DNA
<213> ORGANISM: Vesicular stomatitis indiana virus

<400> SEQUENCE: 15
tatgaaaaaa actaacagat atc                                              23

<210> SEQ ID NO 16
<211> LENGTH: 23
<212> TYPE: DNA
<213> ORGANISM: Vesicular stomatitis indiana virus

<400> SEQUENCE: 16
```

```
tatgaaaaaa agtaacagcg atc                                            23
```

<210> SEQ ID NO 17
<211> LENGTH: 11164
<212> TYPE: DNA
<213> ORGANISM: Vesicular stomatitis indiana virus

<400> SEQUENCE: 17

```
acgaagacaa acaaaccatt attatcatta aaaggctcag gagaaacttt aacagtaatc     60
aaaatgtctg ttacagtcaa gagaatcatt gacaacacag tcatagttcc aaaacttcct    120
gcaaatgagg atccagtgga atacccggca gattacttca aaaatcaaa ggagattcct     180
ctttacatca atactacaaa aagtttgtca gatctaagag atatgtcta ccaaggcctc    240
aaatccggaa atgtatcaat catacatgtc aacagctact tgtatggagc attgaaggac    300
atccggggta agttggataa agattggtca agtttcggaa taaacatcgg aaggcaggg    360
gatacaatcg gaatatttga ccttgtatcc ttgaaagccc tggacggtgt acttccagat    420
ggagtatcgg atgcttccag aaccagcgca gatgacaaat ggttgccttt gtatctactt    480
ggcttataca gagtgggcag aacacaaatg cctgaataca aaaaaggct catggatggg    540
ctgacaaatc aatgcaaaat gatcaatgaa cagtttgaac ctcttgtgcc agaaggtcgt    600
gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctctgcaa ataaccgga    780
atgtctacag aagatgtgac gacctggatc ttgaaccgag aagttgcaga tgagatggtc    840
caaatgatgc ttccaggcca gaaaattgac aaggctgatt catacatgcc ttatttgatc    900
gactttggat tgtcttctaa gtctccatat tcttccgtca aaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgctg acttggcaca acagttttgt gttggagata gcaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaacga   1260
gcagtcatgt cactgcaagg cctaagagag aagacaattg caagtatgc taagtcagag   1320
tttgacaaaa tgaccctata attctcagatc acctattata tattatgcta gctatgaaaa   1380
aaactaacag atatcatgga taatctcaca aaagttcgtg agtatctcaa gtcctattct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatg attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga aacagcctga gcttgaatcc   1740
gacgagcatg gaaagaccct tacggttgac attgccagag gtttaagtgg agagcagaaa   1800
tcccagtggc ttttgacgat taagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt cccaatcaga agccgtatca   1980
gatgtttggt ctctctcaaa gacatccatg actttccaac ccaagaaagc aagtcttcag    2040
```

```
cctctcacca tatccttgga tgaattgttc tcatctagag gagaattcat ctctgtcgga    2100
ggtaacggac gaatgtctca taaagaggcc atcctgctcg gtctgaggta caaaaagttg    2160
tacaatcagg cgagagtcaa atattctctg tagactagta tgaaaaaaag taacagatat    2220
cacaatctaa gtgttatccc aatccattca tcatgagttc cttaaagaag attctcggtc    2280
tgaaggggaa aggtaagaaa tctaagaaat tagggatcgc accacccct tatgaagagg     2340
acactaacat ggagtatgct ccgagcgctc caattgacaa atcctatttt ggagttgacg    2400
agatggacac tcatgatccg aatcaattaa gatatgagaa attcttcttt acagtgaaaa    2460
tgacggttag atctaatcgt ccgttcagaa catactcaga tgtggcagcc gctgtatccc    2520
attgggatca catgtacatc ggaatggcag ggaaacgtcc cttctacaag atcttggctt    2580
ttttgggttc ttctaatcta aaggccactc cagcggtatt ggcagatcaa ggtcaaccag    2640
agtatcatgc tcactgtgaa ggcagggctt atttgccaca cagaatgggg aagacccctc    2700
ccatgctcaa tgtaccagag cacttcagaa gaccattcaa tataggtctt tacaagggaa    2760
cgattgagct cacaatgacc atctacgatg atgagtcact ggaagcagct cctatgatct    2820
gggatcattt caattcttcc aaattttctg atttcagaga gaaggcctta atgtttggcc    2880
tgattgtcga gaaaaaggca tctggagctt gggtcctgga ttctgtcagc cacttcaaat    2940
gagctagtct agcttccagc ttctgaacaa tccccggttt actcagtctc tcctaattcc    3000
agcctttcga caactaata tcctgtcttc tctatcccta tgaaaaaac taacagagat     3060
cgatctgttt ccttgacacc atgaagtgcc ttttgtactt agcttttta ttcatcgggg     3120
tgaattgcaa gttcaccata gttttccac acaaccaaaa aggaaactgg aaaaatgttc     3180
cttccaatta ccattattgc ccgtcaagct cagatttaaa ttggcataat gacttaatag    3240
gcacagcctt acaagtcaaa atgcccaaga gtcacaaggc tattcaagca gacggttgga    3300
tgtgtcatgc ttccaaatgg gtcactactt gtgatttccg ctggtacgga ccgaagtata    3360
taacacattc catccgatcc ttcactccat ctgtagaaca atgcaaggaa agcattgaac    3420
aaacgaaaca aggaacttgg ctgaatccag gcttccctcc tcaaagttgt ggatatgcaa    3480
ctgtgacgga tgctgaagca gcgattgtcc aggtgactcc tcaccatgtg cttgttgatg    3540
aatacacagg agaatgggtt gattcacagt tcatcaacgg aaaatgcagc aatgacatat    3600
gccccactgt cctaactcc acaacctggc attccgacta aaggtcaaa gggctatgtg     3660
attctaacct catttccatg gacatcacct tcttctcaga ggacggagag ctatcatccc    3720
taggaaagga gggcacaggg ttcagaagta actactttgc ttatgaaact ggagacaagg    3780
cctgcaaaat gcagtactgc aagcattggg gagtcagact cccatcaggt gtctggttcg    3840
agatggctga taaggatctc tttgctgcag ccagattccc tgaatgccca gaagggtcaa    3900
gtatctctgc tccatctcag acctcagtgg atgtaagtct cattcaggac gttgagagga    3960
tcttggatta ttccctctgc caagaaacct ggagcaaaat cagagcgggt cttcccatct    4020
ctccagtgga tctcagctat cttgctccta aaaacccagg aaccggtcct gtctttacca    4080
taatcaatgg taccctaaaa actttgaga ccagatacat cagagtcgat attgctgctc     4140
caatcctctc aagaatggtc ggaatgatca gtggaactac cacagaaagg gaactgtggg    4200
atgactgggc tccatatgaa gacgtggaaa ttggacccaa tggagttctg aggaccagtt    4260
caggatataa gtttcctta tatatgattg acatggtat gttggactcc gatcttcatc      4320
ttagctcaaa ggctcaggtg tttgaacatc ctcacattca agacgctgct tcgcagcttc    4380
ctgatgatga gactttattt tttggtgata ctgggctatc caaaaatcca atcgagtttg    4440
```

```
tagaaggttg gttcagtagt tggaagagct ctattgcctc ttttttcttt atcatagggt    4500
taatcattgg actattcttg gttctccgag ttggtattta tctttgcatt aaattaaagc    4560
acaccaagaa aagacagatt tatacagaca tagagatgaa ccgacttgga aagtaactca    4620
aatcctgcac aacagattct tcatgtttga accaaatcaa cttgtgatat catgctcaaa    4680
gaggccttaa ttaaatttta atttttaatt tttatgaaaa aaactaacag caatcatgga    4740
agtccacgat tttgagaccg acgagttcaa tgatttcaat gaagatgact atgccacaag    4800
agaattcctg aatcccgatg agcgcatgac gtacttgaat catgctgatt acaatttgaa    4860
ttctcctcta attagtgatg atattgacaa tttgatcagg aaattcaatt ctcttccgat    4920
tccctcgatg tgggatagta agaactggga tggagttctt gagatgttaa catcatgtca    4980
agccaatccc atctcaacat ctcagatgca taaatggatg ggaagttggt taatgtctga    5040
taatcatgat gccagtcaag ggtatagttt tttacatgaa gtggacaaag aggcagaaat    5100
aacatttgac gtggtggaga ccttcatccg cggctgggc aacaaaccaa ttgaatacat     5160
caaaaaggaa agatggactg actcattcaa aattctcgct tatttgtgtc aaaagttttt    5220
ggacttacac aagttgacat taatcttaaa tgctgtctct gaggtggaat tgctcaactt    5280
ggcgaggact ttcaaaggca agtcagaag aagttctcat ggaacgaaca tatgcaggct     5340
tagggttccc agcttgggtc ctacttttat ttcagaagga tgggcttact tcaagaaact    5400
tgatattcta atggaccgaa actttctgtt aatggtcaaa gatgtgatta tagggaggat    5460
gcaaacggtg ctatccatgg tatgtagaat agacaacctg ttctcagagc aagacatctt    5520
ctcccttcta aatatctaca gaattggaga taaaattgtg gagaggcagg gaaattttc     5580 ttatgacttg attaaaatgg tggaaccgat atgcaacttg aagctgatga aattagcaag    5640
agaatcaagg cctttagtcc cacaattccc tcattttgaa aatcatatca agacttctgt    5700
tgatgaaggg gcaaaaattg accgaggtat aagattcctc catgatcaga taatgagtgt    5760
gaaaacagtg gatctcacac tggtgattta tggatcgttc agacattggg gtcatccttt    5820
tatagattat tacgctggac tagaaaaatt acattcccaa gtaaccatga agaaagatat    5880
tgatgtgtca tatgcaaaag cacttgcaag tgatttagct cggattgttc tatttcaaca    5940
gttcaatgat cataaaaagt ggttcgtgaa tggagacttg ctccctcatg atcatccctt    6000
taaaagtcat gttaaagaaa atacatggcc tacagctgct caagttcaag attttggaga    6060
taaatggcat gaacttccgc tgattaaatg ttttgaaata cccgacttac tagacccatc    6120
gataatatac tctgacaaaa gtcattcaat gaataggtca gaggtgttga acatgtccg     6180 aatgaatccg aacactccta tccctagtaa aaaggtgttg cagactatgt tggacacaaa    6240
ggctaccaat tggaaagaat tcttaaaga gattgatgag aagggcttag atgatgatga     6300
tctaattatt ggtcttaaag gaaaggagag ggaactgaag ttggcaggta gattttttctc  6360 cctaatgtct tggaaattgc gagaatactt tgtaattacc gaatatttga taaagactca    6420
tttcgtccct atgtttaaag gcctgacaat ggcggacgat ctaactgcag tcattaaaaa    6480
gatgttagat tcctcatccg gccaaggatt gaagtcatat gaggcaattt gcatagccaa    6540
tcacattgat tacgaaaaat ggaataacca ccaaaggaag ttatcaaacg gcccagtgtt    6600
ccgagttatg ggccagttct taggttatcc atccttaatc gagagaactc atgaattttt    6660
tgagaaaagt cttatatact acaatggaag accagcttg atgcgtgttc acaacaacac     6720
actgatcaat tcaacctccc aacgagtttg ttggcaagga caagagggtg gactggaagg    6780
```

```
tctacggcaa aaaggatgga gtatcctcaa tctactggtt attcaaagag aggctaaaat    6840
cagaaacact gctgtcaaag tcttggcaca aggtgataat caagttattt gcacacagta    6900
taaaacgaag aaatcgagaa acgttgtaga attacagggt gctctcaatc aaatggtttc    6960
taataatgag aaaattatga ctgcaatcaa aataggaca gggaagttag gacttttgat     7020
aaatgacgat gagactatgc aatctgcaga ttacttgaat tatggaaaaa taccgatttt    7080
ccgtggagtg attagagggt tagagaccaa gagatggtca cgagtgactt gtgtcaccaa    7140
tgaccaaata cccacttgtg ctaatataat gagctcagtt tccacaaatg ctctcaccgt    7200
agctcatttt gctgagaacc caatcaatgc catgatacag tacaattatt ttgggacatt    7260
tgctagactc ttgttgatga tgcatgatcc tgctcttcgt caatcattgt atgaagttca    7320
agataagata ccgggcttgc acagttctac tttcaaatac gccatgttgt atttggaccc    7380
ttccattgga ggagtgtcgg gcatgtcttt gtccaggttt ttgattagag ccttcccaga    7440
tcccgtaaca gaaagtctct cattctggag attcatccat gtacatgctc gaagtgagca    7500
tctgaaggag atgagtgcag tatttggaaa ccccgagata gccaagttcc gaataactca    7560
catagacaag ctagtagaag atccaacctc tctgaacatc gctatgggaa tgagtccagc    7620
gaacttgtta aagactgagg ttaaaaaatg cttaatcgaa tcaagacaaa ccatcaggaa    7680
ccaggtgatt aaggatgcaa ccatatattt gtatcatgaa gaggatcggc tcagaagttt    7740
cttatggtca ataaatcctc tgttccctag atttttaagt gaattcaaat caggcacttt    7800
tttgggagtc gcagacgggc tcatcagtct atttcaaaat tctcgtacta ttcggaactc    7860
ctttaagaaa aagtatcata gggaattgga tgatttgatt gtgaggagtg aggtatcctc    7920
tttgacacat ttagggaaac ttcatttgag aaggggatca tgtaaaatgt ggacatgttc    7980
agctactcat gctgacacat taagatacaa atcctggggc cgtacagtta ttgggacaac    8040
tgtaccccat ccattagaaa tgtgggtcc acaacatcga aaagagactc cttgtgcacc     8100
atgtaacaca tcagggttca attatgtttc tgtgcattgt ccagacggga tccatgacgt    8160
ctttagttca cggggaccat tgcctgctta tctagggtct aaaacatctg aatctacatc    8220
tattttgcag ccttgggaaa gggaaagcaa agtcccactg attaaagag ctacacgtct     8280
tagagatgct atctcttggt ttgttgaacc cgactctaaa ctagcaatga ctatactttc    8340
taacatccac tctttaacag gcgaagaatg gaccaaaagg cagcatgggt tcaaaagaac    8400
agggtctgcc cttcataggt tttcgacatc tcggatgagc catggtgggt tcgcatctca    8460
gagcactgca gcattgacca ggttgatggc aactacagac accatgaggg atctgggaga    8520
tcagaatttc gactttttat tccaagcaac gttgctctat gctcaaatta ccaccactgt    8580
tgcaagagac ggatggatca ccagttgtac agatcattat catattgcct gtaagtcctg    8640
tttgagaccc atagaagaga tcaccctgga ctcaagtatg gactacacgc ccccagatgt    8700
atcccatgtg ctgaagacat ggaggaatgg ggaaggttcg tggggacaag agataaaaca    8760
gatctatcct ttagaaggga attggaagaa tttagcacct gctgagcaat cctatcaagt    8820
cggcagatgt ataggttttc tatatggaga cttggcgtat agaaaatcta ctcatgccga    8880
ggacagttct ctatttcctc tatctataca aggtcgtatt agaggtcgag gtttcttaaa    8940
agggttgcta gacggattaa tgagagcaag ttgctgccaa gtaatacacc ggagaagtct    9000
ggctcatttg aagaggccgg ccaacgcagt gtacggaggt ttgatttact tgattgataa    9060
attgagtgta tcacctccat tccttttctct tactagatca ggacctatta gagacgaatt    9120
agaaacgatt ccccacaaga tcccaacctc ctatccgaca agcaaccgtg atatgggggt    9180
```

```
gattgtcaga aattacttca aataccaatg ccgtctaatt gaaaagggaa aatacagatc    9240
acattattca caattatggt tattctcaga tgtcttatcc atagacttca ttggaccatt    9300
ctctatttcc accacctct tgcaaatcct atacaagcca tttttatctg ggaaagataa     9360
gaatgagttg agagagctgg caaatctttc ttcattgcta agatcaggag aggggtggga    9420
agacatacat gtgaaattct tcaccaagga catattattg tgtccagagg aaatcagaca    9480
tgcttgcaag ttcgggattg ctaaggataa taataaagac atgagctatc ccccttgggg    9540
aagggaatcc agagggacaa ttacaacaat ccctgtttat tatacgacca ccccttaccc    9600
aaagatgcta gagatgcctc caagaatcca aaatcccctg ctgtccggaa tcaggttggg    9660
ccaattacca actggcgctc attataaaat tcggagtata ttacatggaa tgggaatcca    9720
ttacagggac ttcttgagtt gtggagacgg ctccggaggg atgactgctg cattactacg    9780
agaaaatgtg catagcagag gaatattcaa tagtctgtta gaattatcag ggtcagtcat    9840
gcgaggcgcc tctcctgagc cccccagtgc cctagaaact ttaggaggag ataaatcgag    9900
atgtgtaaat ggtgaaacat gttgggaata tccatctgac ttatgtgacc caaggacttg    9960
ggactatttc ctccgactca aagcaggctt ggggcttcaa attgatttaa ttgtaatgga   10020
tatggaagtt cgggattctt ctactagcct gaaaattgag acgaatgtta gaaattatgt   10080
gcaccggatt ttggatgagc aaggagtttt aatctacaag acttatgaa catatatttg    10140 tgagagcgaa aagaatgcag taacaatcct tggtcccatg ttcaagacgg tcgacttagt   10200
tcaaacagaa tttagtagtt ctcaaacgtc tgaagtatat atggtatgta aaggtttgaa   10260
gaaattaatc gatgaaccca atcccgattg gtcttccatc aatgaatcct ggaaaaacct   10320
gtacgcattc cagtcatcag aacaggaatt tgccagagca aagaaggtta gtacatactt   10380
taccttgaca ggtattccct cccaattcat tcctgatcct tttgtaaaca ttgagactat   10440
gctacaaata ttcggagtac ccacgggtgt gtctcatgcg gctgccttaa aatcatctga   10500
tagacctgca gatttattga ccattagcct tttttatatg gcgattatat cgtattataa   10560
catcaatcat atcagagtag gaccgatacc tccgaaccc catcagatg gaattgcaca     10620 aaatgtgggg atcgctataa ctggtataag ctttttggctg agtttgatgg agaaagacat   10680
tccactatat caacagtgtt tagcagttat ccagcaatca ttcccgatta ggtgggaggc   10740
tgtttcagta aaaggaggat acaagcagaa gtggagtact agaggtgatg ggctcccaaa   10800
agatacccga atttcagact ccttggcccc aatcgggaac tggatcagat ctctggaatt   10860
ggtccgaaac caagttcgtc taaatccatt caatgagatc ttgttcaatc agctatgtcg   10920
tacagtggat aatcatttga aatggtcaaa tttgcgaaaa acacaggaa tgattgaatg    10980 gatcaataga cgaatttcaa aagaagaccg gtctatactg atgttgaaga gtgacctaca   11040
cgaggaaaac tcttggagag attaaaaaat catgaggaga ctccaaactt taagtatgaa   11100
aaaaactttg atccttaaga ccctcttgtg gttttattt tttatctggt tttgtggtct     11160
tcgt                                                                 11164
```

<210> SEQ ID NO 18  
<211> LENGTH: 12  
<212> TYPE: DNA  
<213> ORGANISM: Artificial Sequence  
<220> FEATURE:  
<223> OTHER INFORMATION: Description of Artificial Sequence: Synthetic  
     oligonucleotide  
<220> FEATURE:  
<221> NAME/KEY: modified_base

```
<222> LOCATION: (1)..(6)
<223> OTHER INFORMATION: a, c, t, g, unknown or other

<400> SEQUENCE: 18
nnnnnngaga cg                                                   12
```

What is claimed is:

1. A method for rescuing VSV comprising combining a PT7-g10 promoter operably linked to a hammerhead ribozyme sequence a hepatitis delta virus ribozyme sequence, a T7 terminator and a restriction enzyme cleavage site between the ribozyme sequences to increase the efficiency of synthesis and processing of full-length VSV genomic RNA in transfected cells, wherein the genomic sequence of the VSV comprises one or more substitutions at nucleotide positions 1371, 2195, 3039, 7546, and 10959 when aligned with SEQ ID NO: 8.

2. The method of claim 1, wherein the hammerhead ribozyme sequence catalyzes removal of extra nucleotides restoring the authentic 5' terminus of the genomic transcript.

3. The method of claim 1, wherein plasmids to support virus rescue encoding VSV nucleocapsid, phosphoprotein, matrix, glycoprotein and large protein are optimized to improve expression of the trans-acting proteins to initiate virus rescue.

4. The method of claim 3, where the optimization is codon optimization.

5. The method of claim 4, wherein the codon optimization comprises replacing a VSV nucleotide sequence with codons used by highly expressed mammalian genes.

6. The method of claim 4, wherein the codon optimization comprises eliminating potential RNA processing signals in the coding sequence that might direct unwanted RNA splicing or cleavage/polyadenylation reaction, wherein the eliminating comprises:

(a) identifying potential splice site signals and remove by introducing synonymous codons and/or (b) scanning an insert for consensus cleavage/polyadenylation signals (AAUAAA) and introducing synonymous codons to disrupt the consensus cleavage/polyadenylation signals.

7. The method of claim 4, wherein the codon optimization comprises (a) adding a preferred translational start sequence (the Kozak sequence) and/or (b) adding a preferred translational stop codon.

8. The method of claim 4, wherein the codon optimization comprises scanning a sequence for homopolymeric stretches of 5 nucleotides or more and interrupting the sequences by introducing synonymous codons.

9. The method of claim 4, wherein the codon optimization comprises confirming that a modified sequence translates into an expected amino acid sequence.

10. The method of claim 1, wherein the restriction enzyme cleavage site is a BsmB1 restriction enzyme cleavage site.

11. The method claim 1, wherein the substitutions comprise one or more of substitutions selected from:

1371 CA>GC
2195 insert TAG
3039 G>T
7546 C>A
and 10959 AGA>AAA.

12. The method of claim 1, wherein the genomic sequence of the VSV comprises the VSV genomic clone of FIG. 1.

13. A kit for rescuing VSV with increased efficiency, comprising:

(a) A recombinant VSV vector, comprising
  (i) an extended T7 promoter;
  (ii) a polynucleotide sequence encoding a hammerhead ribozyme;
  (iii) a genomic clone of VSV;
  (iv) a polynucleotide sequence encoding a hepatitis delta virus ribozyme;
  (v) a T7 terminator;
wherein the genomic clone of VSV comprises one or more nucleotide substitutions at nucleotide positions 1371, 2195, 3039, 7546, and 10959 when aligned with SEQ ID NO: 8;
and (b) one or more vectors comprising polynucleotide sequences encoding one or more of VSV viral proteins nucleocapsid (N), phosphoprotein (P), matrix (M), glycoprotein (G), and large protein (L).

14. The kit of claim 13, wherein the substitutions comprise one or more of substitutions selected from:

1371 CA>GC
2195 insert TAG
3039 G>T
7546 C>A
and 10959 AGA>AAA.

15. The kit of claim 13, wherein the VSV genomic clone comprises a polynucleotide sequence encoding a VSV protein G partially or completely replaced with SIV or HIV Env.

16. The kit of claim 13, wherein the vectors comprising polynucleotide sequences encoding one or more VSV viral proteins are codon optimized for expression in mammalian cells.

17. The kit of claim 15, wherein the polynucleotide sequences are codon optimized for expression in mammalian cells.

18. The kit of claim 16, wherein the polynucleotide sequences are under control of human cytomegalovirus promoter.

* * * * *